(12) United States Patent
Fenn et al.

(10) Patent No.: US 6,470,217 B1
(45) Date of Patent: Oct. 22, 2002

(54) METHOD FOR HEATING DUCTAL AND GLANDULAR CARCINOMAS AND OTHER BREAST LESIONS TO PERFORM THERMAL DOWNSIZING AND A THERMAL LUMPECTOMY

(75) Inventors: Alan J. Fenn, Wayland, MA (US); John Mon, Silver Spring, MD (US)

(73) Assignee: Celsion Corporation, Columbia, MD (US)

( * ) Notice: Subject to any disclaimer, the term of this patent is extended or adjusted under 35 U.S.C. 154(b) by 0 days.

(21) Appl. No.: 09/548,630

(22) Filed: Apr. 13, 2000

(51) Int. Cl.$^7$ .................................................. A61F 2/00
(52) U.S. Cl. .......................... 607/101; 607/98; 607/102
(58) Field of Search .................... 607/96, 98, 101–102, 607/113, 116; 606/33, 34

(56) References Cited

U.S. PATENT DOCUMENTS 3,895,639 A  *  7/1975  Rodler
4,397,314 A  *  8/1983  Vaguine
4,556,070 A  * 12/1985  Vaguine et al.

(List continued on next page.)

FOREIGN PATENT DOCUMENTS

EP        0 519 415       12/1992

OTHER PUBLICATIONS

International Collaborative Hyperthermia Group, "Radiology With or without Hyperthermia in the Treatment of Superficial Localized Breast Cancer: Results from Five Randomized Controlled Trials", Int. J. Radiation Oncology Biol. Phys., vol. 35, No. 4, pp. 731–744, 1996.*

(List continued on next page.)

Primary Examiner—Roy D. Gibson
(74) Attorney, Agent, or Firm—Venable; Catherine M. Voorhees

(57) ABSTRACT

A method for selectively heating cancerous conditions of the breast including invasive ductal carcinoma and invasive glandular lobular carcinoma, and pre-cancerous conditions of the breast including ductal carcinoma in-situ, lobular carcinoma in-situ, and intraductal hyperplasia, as well as benign lesions (any localized pathological change in the breast tissue) such as fibroadenomas and cysts by irradiation of the breast tissue with adaptive phased array focused microwave energy is introduced. Microwave energy provides preferential heating of high-water content breast tissues such as carcinomas, fibroadenomas, and cysts compared to the surrounding lower-water content normal breast tissues. To focus the microwave energy in the breast, the patient's breast can be compressed and a single electric-field probe, inserted in the central portion of the breast, or two noninvasive electric-field probes on opposite sides of the breast skin, can be used to measure a feedback signal to adjust the microwave phase delivered to waveguide applicators on opposite sides of the compressed breast tissue. The initial microwave power delivered to the microwave applicators is set to a desired value that is known to produce a desired increase in temperature in breast tumors. Temperature feedback sensors are used to measure skin temperatures during treatment to adjust the microwave power delivered to the waveguide applicators to avoid overheating the skin. The microwave energy delivered to the waveguide applicators is monitored in real time during treatment, and the treatment is completed when a desired total microwave energy dose has been administered. By heating and destroying the breast lesion sufficiently, lesions can be reduced in size and surrounding normal breast tissues are spared so that surgical mastectomy can be replaced with surgical lumpectomy or the lesions can be completely destroyed so that surgical mastectomy or lumpectomy is avoided.

28 Claims, 13 Drawing Sheets

U.S. PATENT DOCUMENTS

| | | | | |
|---|---|---|---|---|
| 4,589,423 | A | * | 5/1986 | Turner |
| 4,633,875 | A | | 1/1987 | Turner |
| 4,702,262 | A | * | 10/1987 | Andersen et al. |
| 4,798,215 | A | * | 1/1989 | Turner |
| 5,251,645 | A | * | 10/1993 | Fenn |
| 5,441,532 | A | * | 8/1995 | Fenn |
| 5,540,737 | A | * | 7/1996 | Fenn |
| 5,810,888 | A | * | 9/1998 | Fenn |
| 6,163,726 | A | * | 12/2000 | Wolf .......................... 607/101 |

OTHER PUBLICATIONS

J. van der Zee, et al., "Results of Additional Hyperthermia In Inoperable Pelvic Tumors, Int. Congress on Hyperthermic Oncology", Rome, Italy, pp. 215–217, 1996.*

Jay R. Harris, M.D., et al., "Breast Cancer", New England Journal Of Medicine, vol. 327, pp. 390–398, Aug. 6, 1992.*

Stuart J. Schnitt, M.D., et al, "The Relationship Between Microscopic Margins of Resection and the Risk of Local Recurrence in Patients with Breast Cancer Treated With Breast–Conserving Surgery and Radiation Therapy", vol. 74, No. 6, pp. 1746–1751, Sep. 15, 1994.*

David P. Winchester, M.D., "Standards for Breast–Conservation Treatment", CA–A Cancer Journal for Clinicians, vol. 42, No. 3, pp. 134–162, May/Jun., 1992.*

Charles R. Smart, M.D. et al, "Twenty–Year Follow–Up of the Breast Cancers Diagnosed During the Breast Cancer Detection Demonstration Project", CA–A Cancer Journal for Clinicians, vol. 47, pp. 134–149, May/Jun., 1997.*

Riccardo Valdagni, M.D., et al., "Report of Long–Term Follow–Up In a Randomized Trial Comparing Radiation Therapy and Radiation Therapy Plus Hyperthermia To Metastatic Lymphnodes in Stage IV Head and Neck Patients", I.J. Radiation Oncology Biology Physics, vol. 28, No. 1, pp. 163–169, 1994.

J. Overgaard, et al., Hyperthermia as an Adjuvant to Radiation Therapy of Recurrent or Metastatic Malignant Melanoma. Int. J. Hyperthermia, vol. 12, No. 1, pp. 3–20, 1996.

Eric J. Hall, "Radiobiology for the Radiologist", J.B. Lippincott Company, Fourth Edition, pp. 262–263, 1994.

Carlos A. Perez, et al., "Principles and Practice of Radiation Oncology, Hyperthermia", J.B. Lippincott Company, Second Edition, pp. 396–397, 1992.

Stephen A. Sapareto, Ph.D. et al., "Thermal Dose Determination in Cancer Therapy", A.J. Radiation Oncology Biology Physics., vol. 10, pp. 787–800, 1984.

Arthur R. von Hippel, et al, "Dielectric analysis of Biomaterials", National Technical Information Service, U.S. Department of Commerce, DD Form 1473, pp. 1a–1c, Oct. 1973.

A. von Hippel, A.H. Runck et al., "Dielectric Analysis of Biomaterials", Massachusetts Institute of Technology, pp. i–ii, and 1–20, Oct., 1973.

Merrill I. Skolnik, "Introduction to Radar systems", McGraw–Hill, Inc., pp. 332–333, 1980.

R.T. Compton, Jr., "Adaptive Antennas Concepts and Performance", Prentice–Hall, Inc., p. 1, 1988.

Alan J. Fenn, "Evaluation of Adaptive Phased Array Antenna Far–Field Nulling Performance in the Near–Field Region", IEEE Transactions on Antennas and Propagation, vol. 38, No. 2, pp. 173–185, Feb., 1990.

H. Bassen, et al, "Evaluation of an Implantable Electric–Field Probe Within Finite Simulated Tissues", American Geophysical Union, vol. 12, No. 6(s), pp. 25 Nov.–Dec. 1977.

Alan J. Fenn, et al., "Adaptive Radiofrequency Hyperthermia–Phased Array System for Improved Cancer Therapy: Phantom Target Measurements", Int. J. Hyperthermia, vol. 10, No. 2, pp. 189–208, 1994.

Alan J. Fenn, et al., "Improved Localization of Energy Deposition in Adaptive Phased–Array Hyperthermia Treatment of Cancer", The Journal of Oncology Management, pp. 22–29, Mar./Apr., 1998.

Alan J. Fenn, Ph.D., "Adaptive Focusing Experiments With an Air–Cooled 915–MHz Hyperthermia Phased Array For Deep Heating of Breast Carcinomas", Massachusetts Institute of Technology, Surgical Application of Energy Sources, pp. 1–4, May 17–19, 1996.

Alan J. Fenn, et al., "An Adaptive Microwave Phased Array for Targeted Heating of Deep Tumors in Intact Breast: Animal Study Results", Int. J. Hyperthermia, vol. 15, No. 1, pp. 45–61, 1999.

L. R. Gavrilov, et al., "Pre–clinical Evaluation of a Two–Channel Microwave Hyperthermia System with Adaptive phase Controlling a Large Animal", Int. J. Hyperthermia, vol. 15, No. 6, pp. 495–507, 1999.

G.M. Samaras, et al., "Production of Controlled Hyperthermia Fields for Cancer Therapy", Urban & Schwarzenberg, pp. 131–132, 1978.

A. Y. Cheung, et al., "Dual–Beam TEM Applicator for Direct–Contact Heating of Dielectrically Encapsulated Malignant Mouse Tumor", The American Geophysical Union, vol. 12, No. 6(S), pp. 81–85, Nov.–Dec., 1997.

National Council on Radiation Protection and Measurements, Mammography—A User's Guide', Report No. 85, p. 6, Mar. 1, 1986.

Susan M. Love, M.D., et al., "Dr. Susan Love's Breast Book", Addison–Wesley Publishing Company, Inc., pp. 191–196, 1990.

S.S. Chaudhary, et al., "Dielectric Properties of Normal & Malignant Human Tissues at Radiowave & Microwave Frequencies", Indian Journal of Biochemistry & Biophysics, vol. 21, pp. 76–79, Feb. 1984.

William T. Joines, et al, "The Measured Electrical Properties of Normal and Malignant Human Tissues from 50 to 900 MHz", Med. Physics, vol. 21, No. 4, pp. 547–550, 1994.

Andrzej J. Surowiec, et al, "Dielectric Properties of Breast Carcinoma and the Surrounding Tissues" IEEE Transactions on Biomedical Engineering, vol. 35, No. 4, pp. 257–263, Apr. 1988.

A. M. Campbell, et al., "Dielectric Properties of Female Human Breast Tissue Measured in Vitro at 3.2 GHz", Phys. in Med and Biol., vol. 37, No. 1, pp. 193–210, 1992.

Everett C. Burdette, "Electromagnetic and Acoustic Properties of Tissues", AAPM Medical Physics Monographs No. 8, pp. 105, 130, 1982.

S. Gabriel, et al., "The Dielectric Properties of Biological Tissues; III. Parametric Models for the Dielectric Spectrum of Tissues", Phys. Med. Biol., vol. 41, pp. 2271–2293, 1996.

Lawrence Bassett, M.D., et al., "Stereotactic Core–Needle biopsy of the Breast: A Report of the Joint Task Force of the American College of Radiology American College of Radiology College of Surgeons, and College of American Pathologists", CA Cancer Journal Clinicians, vol. 47, pp. 171–190, May/Jun. 1997.

Daniel C. Sullivan, M.D., et al., "Measurement of Force Applied During Mammography", Duke University, Department of Radiology, pp. 355–357, Dec. 18, 1988.

Dr. Michael Gautherie, (Editor), "Methods of External Hyperthermic Heating", Springer–Verlag, New York, p. 33, 1990.

Alan J. Fenn, et al., "Minimally Invasive Monopole Phased Arrays for Hyperthermia Treatment of Breast Carcinomas: Design and Phantom Tests", Presented at the 1994 International Symposium on Electromagnetic Compatibility, pp. 566–569, May 17–19, 1994.

S. B. Field, et al., "An Introduction to the Practical Aspects of Clinical Hyperthermia", Taylor & Francis, pp. 263, 290, 1990.

David Vitrogan, "Elements of Electric and Magnetic Circuits", Rinehart Press, pp. 31–33, 1971.

Allen Taflove, "Advances in Computational Electrodynamics", Artech House, Norwood, Massachusetts, p. 642, 1998.

* cited by examiner

METHOD FOR HEATING DUCTAL AND GLANDULAR CARCINOMAS AND OTHER BREAST LESIONS TO PERFORM THERMAL DOWNSIZING AND A THERMAL LUMPECTOMY

BACKGROUND OF THE INVENTION

The present invention generally relates to a minimally invasive method for administering focused energy such as adaptive microwave phased array hyperthermia for treating ductal and glandular carcinomas and intraductal hyperplasia as well as benign lesions such as fibroadenomas and cysts in compressed breast tissue. In addition, the method according to the invention may be used to treat healthy tissue containing undetected microscopic pathologically altered cells of high-water content to prevent the occurrence of or the recurrence of cancerous, pre-cancerous or benign breast lesions.

In order to treat primary breast cancer with hyperthermia, it is necessary to heat large volumes of tissue such as a quadrant or more of the breast. It is well known that approximately 90% of all breast cancers originate within the lactiferous ductal tissues (milk ducts) with much of the remaining cancers originating in the glandular tissue lobules (milk sacks) (Harris et al., The New England Journal of Medicine, Vol. 327, pp. 390–398, 1992). Breast carcinomas often involve large regions of the breast for which current conservative treatments have a significant risk of local failure. Schnitt et al., Cancer, Vol. 74 (6) pp. 1746–1751, 1994. With early-stage breast cancer, known as T1 (0–2 cm), T2 (2–5 cm) cancers, the entire breast is at risk and often is treated with breast-conserving surgery combined with full-breast irradiation to destroy any possible microscopic (not visible to the human eye without the aid of a microscope or mammography) cancer cells in the breast tissue (Winchester et al., CA-A Cancer Journal for Clinicians, Vol. 42, No. 3, pp. 134–162, 1992). The successful treatment of invasive ductal carcinomas with an extensive intraductal component (EIC) where the carcinomas have spread throughout the ducts is particularly difficult, since large portions of the breast must be treated. Over 800,000 breast needle biopsies of suspicious lesions are performed annually in the United States with approximately 180,000 cases of cancer detected, the rest being nonmalignant such as fibroadenomas and cysts.

The use of heat to treat breast carcinomas can be effective in a number of ways, and in most cases the heat treatment must be capable of reaching, simultaneously, widely separated areas within the breast. Heating large volumes of the breast can destroy many or all of the microscopic carcinoma cells in the breast, and reduce or prevent the recurrence of cancer—the same approach is used in radiation therapy where the entire breast is irradiated with x-rays to kill all the microscopic cancer cells. Heating the tumor and killing a large percentage or all of the tumor cells prior to lumpectomy may reduce the possibility of inadvertently seeding viable cancer cells during the lumpectomy procedure, thus reducing local recurrences of the breast. Sometimes, the affected breast contains two or more tumor masses distributed within the breast, known as multi-focal cancer, and again the heating field must reach widely separated regions of the breast. Locally advanced breast carcinomas (known as T3) (Smart et al., A Cancer Journal for Clinicians, Vol. 47, pp. 134–139, 1997) can be 5 cm or more in size and are often treated with mastectomy. Pre-operative hyperthermia treatment of locally advanced breast cancer may shrink the tumor sufficiently to allow a surgical lumpectomy procedure to be performed—similar to the way pre-operative chemotherapy is currently used. Pre-operative hyperthermia treatment of locally advanced breast cancer may destroy the tumor completely, eliminating the need of any surgery.

It is well known that microwave energy can preferentially heat high-water content tissues such as breast tumors and cysts, compared to the heating that occurs in low-water content tissue such as fatty breast tissue. Many clinical studies have established that hyperthermia (elevated temperature) induced by electromagnetic energy absorption in the microwave band, significantly enhances the effect of radiation therapy in the treatment of malignant tumors in the human body (Valdagni, et al., International Journal of Radiation Oncology Biology Physics, Vol. 28, pp. 163–169, 1993; Overgaard et al., International Journal of Hyperthermia, Vol. 12, No. 1, pp. 3–20, 1996; Vernon et al., International Journal of Radiation Oncology Biology Physics, Vol. 35, pp. 731–744, 1996; van der Zee et al, Proceedings of the $7^{th}$ International Congress on Hyperthermic Oncology, Rome, Italy, April 9–13, Vol. 11, pp. 215–217, 1996). Radio-resistant cells such as S-phase cells can be killed directly by elevated temperature (Hall, Radiobiology for the Radiologist, $4^{th}$ Edition, JB Lippincott Company, Philadelphia, pp. 262–263, 1994; Perez and Brady, Principles and Practice of Radiation Oncology, Second Edition, JB Lippincott Company, Philadelphia, pp. 396–397, 1994). Hyperthermia treatments with microwave radiating devices are usually administered in several treatment sessions, in which the malignant tumor is heated to about 430° C. for about 60 minutes. It is known that the amount of time to kill tumor cells decreases by a factor of two for each degree increase in temperature above about 43° C. (Sapareto, et al., International Journal of Radiation Oncology Biology Physics, Vol. 10, pp. 787–800, 1984). Thus, a 60-minute treatment at 43° C. can be reduced to only about 15 minutes at 45° C., which is often referred to as an equivalent dose ($t_{43° C.}$ equivalent minutes). During treatments with noninvasive microwave applicators, it has proven difficult to heat semi-deep tumors adequately while preventing surrounding superficial healthy tissues from incurring pain or damage due to undesired hot spots. The specific absorption rate (SAR) in tissue is a common parameter used to characterize the heating of tissue. The SAR is proportional to the rise in temperature over a given time interval times the specific heat of the tissue and for microwave energy the SAR is also proportional to the electric field squared times the tissue electrical conductivity. The units of absolute SAR are watts per kilogram.

Incoherent-array or non-adaptive phased array hyperthermia treatment systems typically are restricted in their use for heating deep tissue, because they tend to overheat intervening superficial tissues, which can cause pain and/or burning. The first published report describing a non-adaptive phased array for deep tissue hyperthermia was a theoretical study (von Hippel, et al., Massachusetts Institute of Technology, Laboratory for Insulation Research, Technical Report 13, AD-769 843, pp. 16–19, 1973). U.S. Pat. No. 3,895,639 to Rodler describes two-channel and four-channel non-adaptive phased away hyperthermia circuits. Recent developments in hyperthermia systems effectively targets the delivery of heat to deep tissue using adaptive phased array technology originally developed for microwave radar systems (Skohuk, Introduction to Radar Systems, Second Edition, McGraw-Hill Book Company, 1980 pp. 332–333; Compton, Adaptive Antennas, Concepts and Performance, Prentice Hall, New Jersey, p. 1 1988; Fenn, IEEE Transactions on Antennas and Propagation, Vol. 38, number 2, pp. 173–185, 1990; U.S. Pat. Nos. 5,251,645; 5,441,532; 5,540,737; 5,810,888).

Bassen et al., Radio Science, Vol. 12, No. 6(5), November–December 1977, pp. 15–25, shows that an electric-field probe can be used to measure the electric-field pattern in tissue, and in particular, shows several examples in which the measured electric-field has a focal peak in the central tissue. This paper also discusses a concept for real-time measurements of the electric-field in living specimens. However, Bassen et al. did not develop the concept of measuring an electric field using real-time with an electric-probe to adaptively focus a phased array.

An adaptive phased array hyperthermia system uses E-field feedback measurements to focus its microwave energy on deep tissue while simultaneously nullifying any energy that might overheat surrounding healthy body tissue. Pre-clinical studies indicate that adaptive microwave phased arrays have the potential for delivering deep heat while sparing superficial tissues from excessive temperatures in deep torso (Fenn, et al., International Journal of Hyperthermia, Vol. 10, No. 2, March–April, pp. 189–208, 1994; Fenn et al., The Journal of Oncology Management, Vol. 7, number 2, pp. 22–29, 1998) and in breast (Fenn, Proceedings of the Surgical Applications of Energy Sources Conference, 1996; Fenn et al., International Journal of Hyperthermia, Vol. 15, No. 1, pp. 45–61, 1999; Gavrilov et al., International Journal of Hyperthermia, Vol. 15, No. 6, pp. 495–507, 1999).

The most difficult aspect of implementing hyperthermia in deep breast tissues, with microwave energy, is producing sufficient heating at a predetermined depth while protecting the skin from burns. Noninvasive multiple applicator adaptive microwave phased arrays with invasive and noninvasive electric field probes can be used for producing an adaptively focused beam at the tumor position with adaptive nulls formed in healthy tissues as described in U.S. Pat. Nos. 5,251,645, 5,441,532, 5,540,737, and 5,810,888, all of which are incorporated herein by reference. Ideally, a focused microwave radiation beam is concentrated at the tumor with minimal energy delivered to surrounding healthy tissue. To control the microwave power during treatment, a temperature-sensing feedback probe (Samaras et al., Proceedings of the $2^{nd}$ International Symposium, Essen, Germany, June 2–4, 1977, Urban & Schwarzenberg, Baltimore, 1978, pp. 131–133) is inserted into the tumor, however, it is often difficult to accurately place the probe in the tumor. An additional difficulty occurs in delivering hyperthermia to carcinoma spread throughout the ductal or glandular tissues of the breast, because of a lack of a well defined target position for the temperature-sensing feedback probe. In other situations, it is desirable simply to avoid inserting probes (either temperature or E-field) into the breast tissue in order to reduce the risk of infection or spreading the cancer cells when the probe passes through the tumor region or when it is undesirable for the probe to penetrate the lesion such as a cyst.

The standard of medical care for treating benign cysts that have been detected varies from doing noting to draining the cysts. The medically accepted position of not treating the cysts exists because the only known method of removing cysts involves invasive surgery. The alternative to surgically cutting and removing a cyst is draining the cyst. Draining the cyst is achieved by piercing the cyst and removing the liquid inside the cyst. While this method may temporarily relieve the pain associated with the cyst, the cyst may grow back if the draining procedure failed to remove the entire cyst. Therefore, there is a need for a non-invasive removal of these benign cysts.

SUMMARY OF THE INVENTION

The above problems are solved by the method for heating cancerous or benign conditions of the breast according to the invention which comprises the steps of inserting an E-field probe sensor in the breast, monitoring temperatures of the skin surface, orienting two microwave applicators on opposite sides of the breast, setting the initial microwave power and phase delivered to each microwave applicator in order to focus the field at the inserted E-field sensor, adjusting the microwave power to be delivered to the breast based on the monitored skin temperatures, and monitoring the microwave energy dose delivered to the breast being treated and completing the treatment when a desired total microwave energy dose has been delivered by the microwave applicators.

Moreover, the method according to the invention has application in situations such as when there is no well-defined position to place the temperature feedback sensor, or when it is desirable to avoid inserting a temperature probe into the breast tissue. Only a single sly minimally invasive E-field sensor is required in the preferred method according to the invention. Thus, in the case of advanced breast cancer (e.g., a tumor 5–8 cm), the inventive method can destroy a significant portion of the breast cancer cells and shrink the tumor or lesion (i.e., thermal downsizing to e.g., 2–3 cm) thereby replacing a surgical mastectomy with a surgical lumpectomy. In the alternative, the entire advanced breast cancer lesion can be destroyed (i.e., a thermal mastectomy) and no surgery may be required. In early-stage breast cancer or for small breast lesions, the inventive method may destroy all of the breast cancer cells or benign lesions with heat (i.e., a thermal lumpectomy) thereby avoiding a surgical lumpectomy. In addition, the method ran be used to enhance radiation therapy or for targeted dog delivery with thermosensitive liposomes as described in U.S. Pat. No. 5,810,888 and/or targeted gene therapy delivery.

The method according to the invention destroys the cancerous cells while sparing the normal glandular, ductal, connective, and fatty tissue of the breast. Thus, a thermal lumpectomy according to the invention avoids damage to such healthy tissue and is a breast conservation technique.

The breast skin surface can be measured by attaching temperature probe sensors to the skin surface of the breast. Alternatively, the skin surface (as well as internal breast tissue) temperature can be monitored by other external means, including infrared, laser ultrasound, electrical impedance tomography magnetic resonance imaging, and radiometry techniques as known in the art Alternatively, a temperature probe could be inserted at an appropriate depth in the breast tissue to monitor the temperature thereof. As discussed below, insertion of a temperature probe is not a preferred embodiment.

The method according to the invention can be achieved with or without breast compression. In a preferred method, a patient's breast would be compressed between 3 and 8 cm with compression plates. The microwave applicators would be oriented on exterior sides of the compression plates (ie., the sides of the compression plates away from the breast).

As described below, recent clinical measured data for compressed, living breast tissue supports applicants' inventive step of monitoring the microwave energy dose delivered to the breast being treated and completing the treatment based on the total microwave energy dose that has been received. That is, conventional temperature feedback measurements of tumor thermal dose can be replaced with the total microwave energy delivered to the phased array microwave applicators. Accordingly, with the instant invention, instead of temperature feedback measurements which require the insertion of a temperature feedback probe into the breast and its inherent problems, microwave energy dose is used as feedback to determine the required length of treatment In this application the term "microwave energy dose" (in Joules or watt-seconds) is similar to the dose used in radiation therapy, namely the radiation absorbed dose (Rad) which is a unit of absorbed dose of radiation defined as deposition of 100 ergs of energy per gram of tissue.

Thus, the instant method for selectively heating cancerous conditions of the breast avoids the risk of spreading cancer cells since the temperature probe is not inserted into the treated area (tumor bed) of the breast. The elimination of an inserted temperature probe reduces the risk of infection to a patient as a result of the inserted probe. Likewise, the microwave field applied to a tumor would not be subjected to scattering or other disturbance caused by a temperature probe, especially a metallic probe. In addition, the time and costs associated with inserting the temperature probe are saved.

The inventive method may also be used to treat healthy breast tissue or undetected high-water content microscopic precancerous or pre-benign cells in seemingly healthy breast tissue to prevent the occurrence of or recurrence of cancerous conditions of the breast. The cancerous conditions that can be prevented include invasive ductal and lobular carcinoma and pre-cancerous conditions of the breast including ductal carcinoma in-situ, lobular carcinoma in-situ, and intraductal hyperplasia and benign lesions (such as cysts and fibroadenomas). Thus, the method according to the invention would be able to destroy microscopic precancerous or pre-benign cells before they are detected. This would be an early treatment that could prevent cancer before it is detected. In the case of healthy tissue, the breast tissue would be irradiated with microwave energy focused at high-water content microscopic cells that are known to form lesions.

In a preferred method, the patient lies prone with the breast pendulant through a hole in the treatment table and the treated breast is compressed with flat plastic compression plates which immobilizes the breast tissue, reduces blood flow, and reduces the penetration depth required for the microwave radiation. The breast compression plates are made of a microwave transparent plastic material, and contain one or more apertures to allow imaging of breast tissues and placement of a minimally invasive E-field feedback probe at the desired focal depth. The placement of an E-field feedback probe may be achieved with an ultrasound transducer or other type of image guidance.

Two microwave air-cooled waveguide applicators (such as described by Cheung et al., Radio Science, Vol. 12, No. 6(S), November–December 1977, pp. 81–85.) are positioned on opposite sides of the compression plates. A phased away can be achieved with a multiple number of applicators greater than or equal to two. In a preferred embodiments coherent 915 MHz microwave power is delivered to the two waveguide applicators, at a predetermined power level, while phase shifters in each channel are adjusted to maximize and focus the microwave energy at the E-field probe sensor. The air flow from individual fans surrounding the breast or from fans mounted in the applicator waveguides may be adjusted. The airflow cooling the waveguide applicators would go through the applicators. The air for cooling the waveguide applicators may be refrigerated, air-conditioned or room temperature. Water-cooled waveguide applicators may be substituted for air-cooled applicators, as one of ordinary skill in the art would recognize.

During the hyperthermia treatment, the microwave power level delivered to each of the applicators may be adjusted either manually or automatically to control the skin temperatures to avoid high temperatures that could cause skin burns or blisters. In addition, the amount of breast compression by compression plates, if used, is adjusted as necessary during treatment to provide patient comfort. Each time the breast compression is adjusted or the breast repositioned, the microwave-energy, phased array is refocused so that the E-field probe sensor receives maximum power. The total microwave energy, since the start of the treatment, delivered to the microwave applicators is monitored during the treatment. The treatment is completed when a desired amount of total microwave energy is delivered to the microwave applicators, which indicates that the breast lesion cells are significantly (i.e., thermal downsizing) or completely destroyed (i.e., thermal lumpectomy).

In order to determine the effectiveness of the treatment, the breast tissue may be imaged and examined with mammography means including x-ray, ultrasound, and magnetic resonance imaging before and after the microwave total energy dose is administered, as well as with pathological results from needle biopsy of the breast tissues.

In an alternate embodiment of the invention, the single invasive E-field sensor is replaced with two E-field sensors positioned on opposite sides of the breast skin surface and the array is phase focused by minimizing (nulling) the combined power received by the two sensors, providing a completely noninvasive treatment. Algorithms are used in conjunction with the feedback signals sensed by the E-field skin sensors to null areas on the outside thereby focussing the applied energy on an internal site.

Such a totally non-invasive hyperthermia treatment where E-field probes and temperature sensors monitor the breast skin surface would provide an effective method of destroying benign cysts and the pain associated therewith. Thus, applicants' inventive method is envisioned as treating or destroying detected benign cysts.

While the preferred embodiment is described with reference to adaptive microwave phased array technology, Applicants' method may be achieved by focussing energy, in general, to heat and ablate an area of tissue. The focused energy may include electromagnetic waves ultrasound waves or waves at radio frequency. That is, applicants' inventive method includes any energy that can be focused to heat and ablate an area of tissue.

In yet another embodiment of the invention, the boundary of an area of tissue to be treated in a body (e.g., breast) is calculated, an E-field probe may be inserted in the body or at least two E-field sensors are positioned on the outside of the body; and energy is applied through applicators to the area to be treated. In this embodiment, the focus of the energy would change so that the focus scans the area to be treated. That is, there is no longer a fixed focus spot as the relative phase of the applied energy would be adjusted so that the focus moves inside the area to be treated thereby obtaining a geometric shape of heating.

A fixed focus spot is determined through the appropriate algorithm. Then, for example, the relative phase of the applicators to obtain this fixed focus spot is adjusted 30° one way and then 30° the other way to "scan" a larger heated/treated area. Depending on the size of the area to be treated the scan may focus between 180° and 90° or 60° or 120°.

Further objectives and advantages will become apparent from a consideration of the description and drawings.

BRIEF DESCRIPTION OF THE DRAWINGS

The invention is better understood by reading the following detailed description with reference to the accompanying figures, in which like reference numerals refer to like elements throughout, and in which.

DETAILED DESCRIPTION OF THE PREFERRED EMBODIMENTS

Dielectric Properties of Breast Tissue

Figure 1:
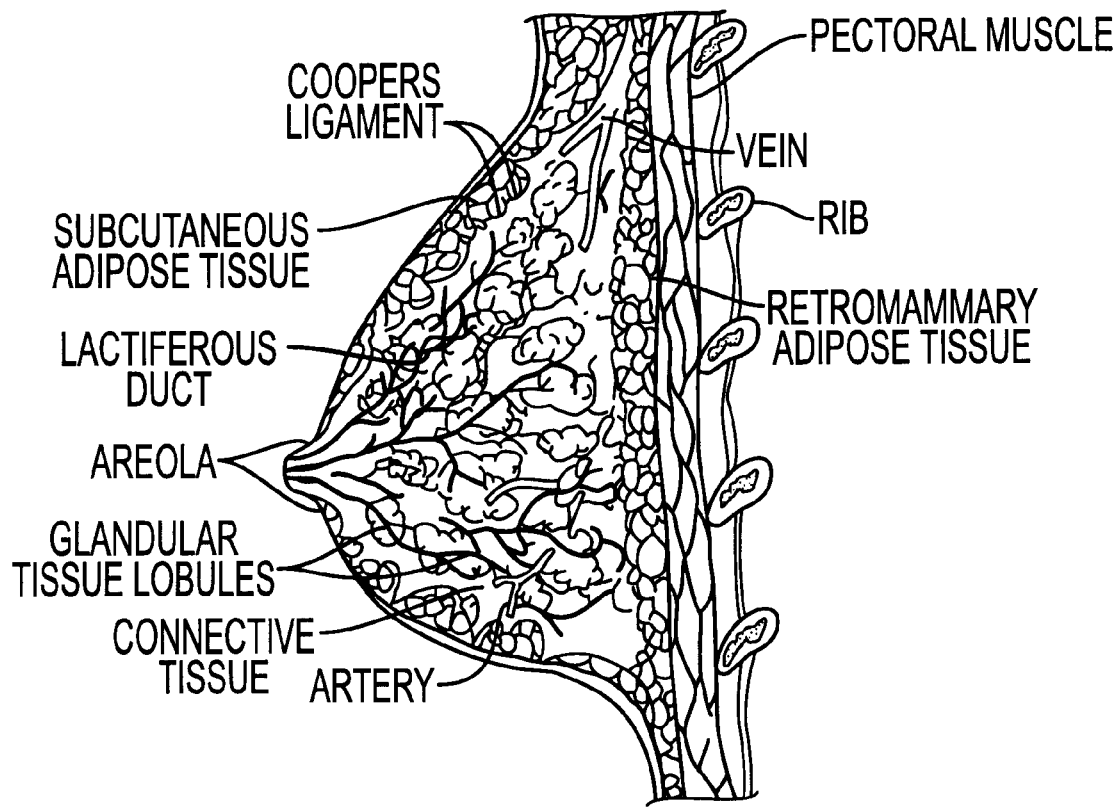
FIG. 1 is a detailed lateral view of the female breast.
Figure 2:
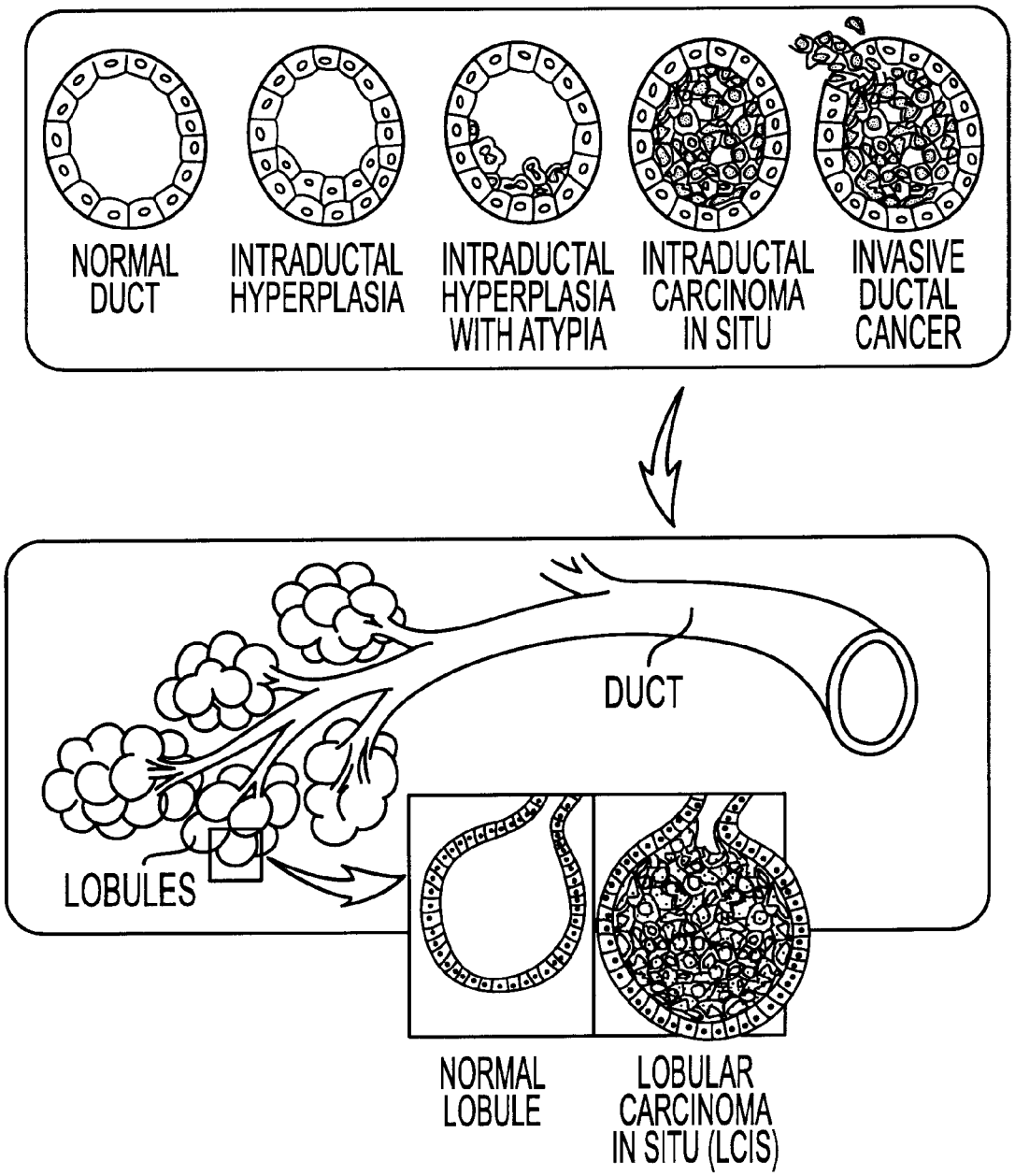
FIG. 2 shows examples of the progression of ductal carcinomas and lobular carcinomas in the ductal and glandular tissues of the breast.

A detailed lateral view of the female breast is shown in FIG. 1 (Mammography—A User's Guide, National Council on Radiation Protection and Measurements, NCRP Report No. 85, 1 August 1987, p.6). The amount of glandular and fatty tissue within the breast can vary widely, from primarily fatty tissue to extremely dense glandular tissue. Breast cancer cells, which are high-water content cells, usually form within the lactiferous ducts and glandular tissue lobules as depicted in FIG. 2 (adapted from Dr. Susan Love's Breast Book, Addison Wesley, Mass., 1990, pp. 191–196). The first indication of abnormal cell growth within the duct is referred to as intraductal hyperplasia, followed by intraductal hyperplasia with atipia. When the ducts become nearly full, the condition is known as intraductal carcinoma in situ (DCIS). These three conditions are referred to as pre-cancers. Finally, when the ductal carcinomas break through the ductal wall, the lesion is referred to as invasive ductal cancer. Cancer forms in the same way in the glandular lobules of the breast. All of the above cells are often cited as being high-water content with the exception of pure fat tissue (low-water content) and pure glandular/connective tissue (low to medium-water content) within the breast.

Figure 3:
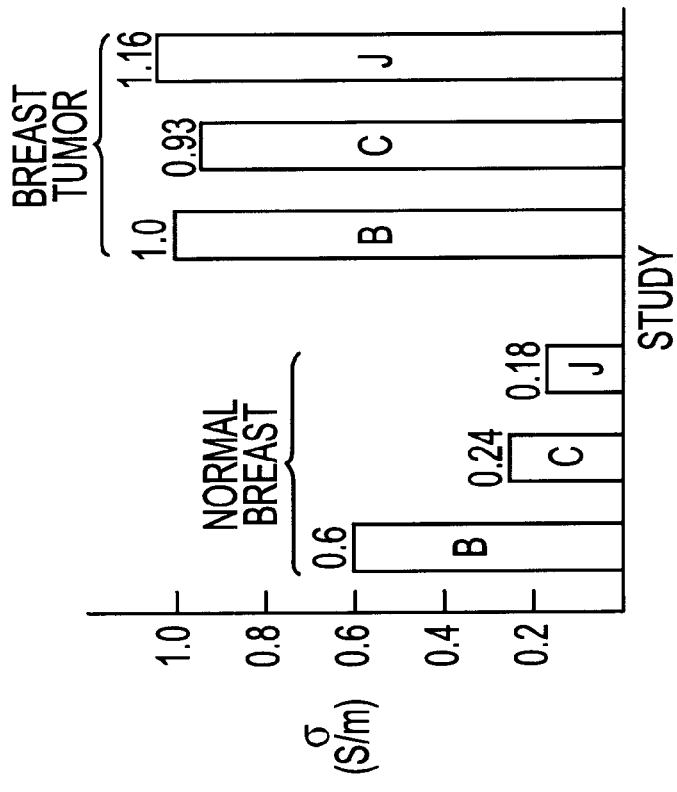
FIG. 3 shows the measured values of dielectric constant and electrical conductivity for normal breast tissue and breast tumor for three different studies. The study labeled B (Burdette) was for measurements through the breast skin which accounts for the differences between the other studies, denoted C and J.
Figure 3:
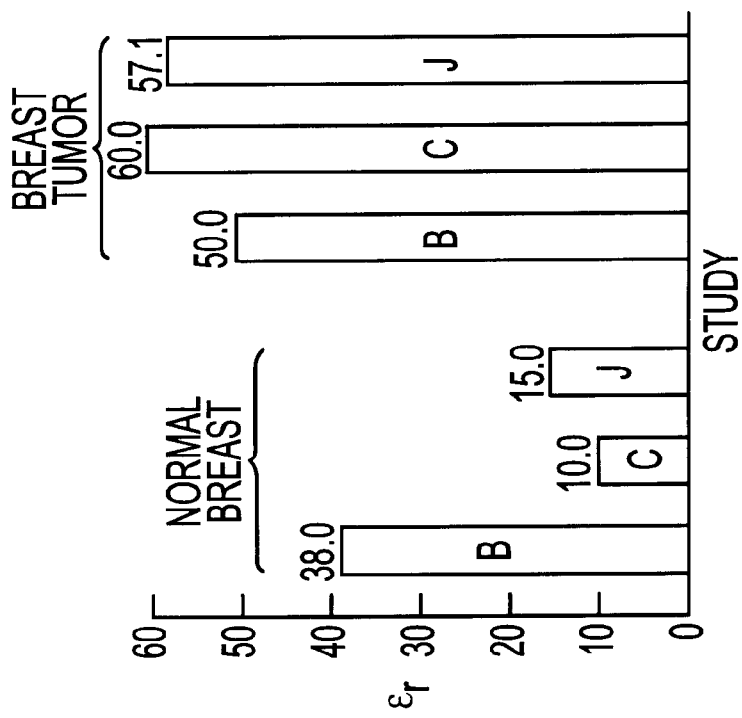

Microwave radiation in the Industrial, Scientific, Medical (ISM) band 902 to 928 MHz is commonly used in commercial clinical hyperthermia systems, and is the primary frequency band considered here. Very little detailed microwave heating information on female breast tissues exists—however, it is well known that carcinomas of the breast are selectively heated compared to surrounding normal breast tissues. Four main articles are: 1) Chaudliary et al., Indian Journal of Biochemistry and Biophysics, Vol. 21, pp. 76–79, 1984; 2) Joines et al., Medical Physics, Vol. 21, No. 4, pp. 547–550, 1994; 3) Surowiec et al., IEEE Transactions on Biomedical Engineering, Vol. 35, No. 4, pp. 257–263, 1988 and 4) Campbell and Land, Physics in Medicine an Biology, Vol. 37, No. 1, 193–210, 1992. Another article, Burdette, AAPM Medical Physics Monographs, No. 8, pp. 105, 130, 1982, has measured data for breast tissue, however, these data were measured through the skin and probably are not representative of breast tissue itself. The dielectric properties are usually given in terms of dielectric constant and electrical conductivity as depicted for normal breast tissue and breast tumor as shown in FIG. 3. At 915 MHz, removing the data from the Burdette study, the average dielectric constant of normal breast is 12.5 and the average conductivity is 0.21 S/m. In contrast, for breast tumor the average dielectric constant is 58.6 and the average conductivity is 1.03 S/m. Note: The data from Chaudhary et al (C) and Joines et al (J) studies are measured at room temperature (25° C.). It should be noted that as temperature increases, generally the dielectric constant decreases and the electrical conductivity increases. The dielectric parameters of normal breast and breast tumor are similar to low-water content fatty tissue and high-water content muscle tissue, respectively. It should be noted that normal breast tissue contains a mixture of fat, glandular and connective tissues. Detailed information on 17 tissue types, including skin, muscle, and fat, is presented in an article by Gabriel et al, Phys. Med. Biol., Vol. 41, pp. 2271–2293, 1996. The article by Surowiec et al., has detailed information on selected glandular, ductal, fatty and cancerous tissues, but they only measured the parameters in the range 20 KHz to 100 MHz. It is possible to estimate the electrical properties of breast tissues at 915 MHz from data measured at 100 MHz. Applicants are not aware of any measured dielectric parameter data on pure ductal and glandular breast tissue for the frequency of interest, namely 915 MHz.

Figure 4:
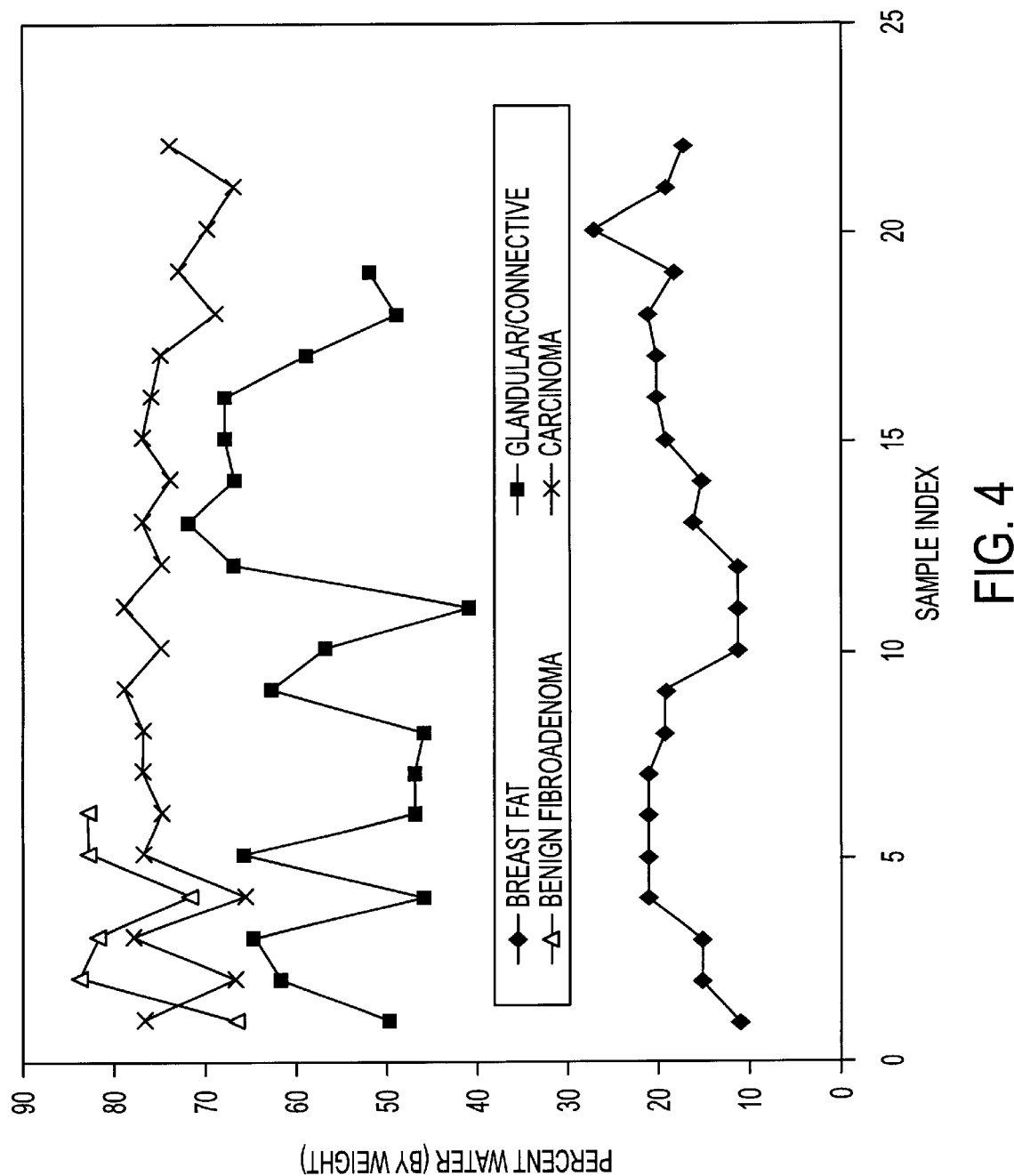
FIG. 4 shows the measured water content of breast fat, glandular/connective tissue, benign Fibroadenoma, and breast carcinoma (from Campbell and Land 1992)

The article by Campbell and Land has measured dielectric parameter data at 3.2 GHz, and the percent water content of breast fat, glandular and connective tissue, benign tumors (including fibroadenomas), and malignant tumors. Their measured data of percent water content can be used to assess the relative heatability of breast tissues, that is, higher water content tissues heat faster than lower water content tissues. The range of values for measured water content (by weight) is as follows: breast fat (11 to 31%), glandular and connective tissue (41 to 76%), benign tumors (62 to 84%), and malignant tumors (66 to 79%) where selected values are depicted in FIG. 4. Thus based on water content, it is expected that benign breast lesions and breast tumors will heat significantly faster than glandular, connective, and fatty breast tissues. Typically, for electrical conductivity at 3.2 GHz, their best choice of measured values is as follows: breast fat (0.11 to 0.14 S/m), glandular and connective tissue (0.35 to 1.05 S/m), benign tumors (1.0 to 4.0 S/m), and malignant tumors (3.0 to 4.0 S/m). Accordingly, the electrical conductivity of benign and malignant tumors tends to be up to about four times higher than the glandular and connective tissue and to about 30 times higher than pure fat. These data are consistent with the electrical conductivity data measured at 915 MHz by Chaudhary et al. as well as by Joines et al shown in FIG. 3.

Moreover, Chaudhary 1984 has measured electrical conductivity data for normal breast tissue at 3 GHz, where the conductivity is 0.36 S/m, consistent with the range (0.35 to 1.05 S/m) for normal glandular and connective tissue measured by Campbell and Land at 3.2 GHz. Thus, from the best available data, breast fat is low-water content, glandular and connective tissue is low to medium-water content, and breast tumors are high-water content. Accordingly, it is expected that benign and malignant tumor cells will be heated much more rapidly and to significantly higher temperatures than the surrounding fat, glandular, ductal, and connective tissue cells. In other words, only the microscopic and visible tumor cells are preferentially heated in this treatment, with all the surrounding fat, glandular, ductal, and connective tissues spared from heat damage.

Figure 5:
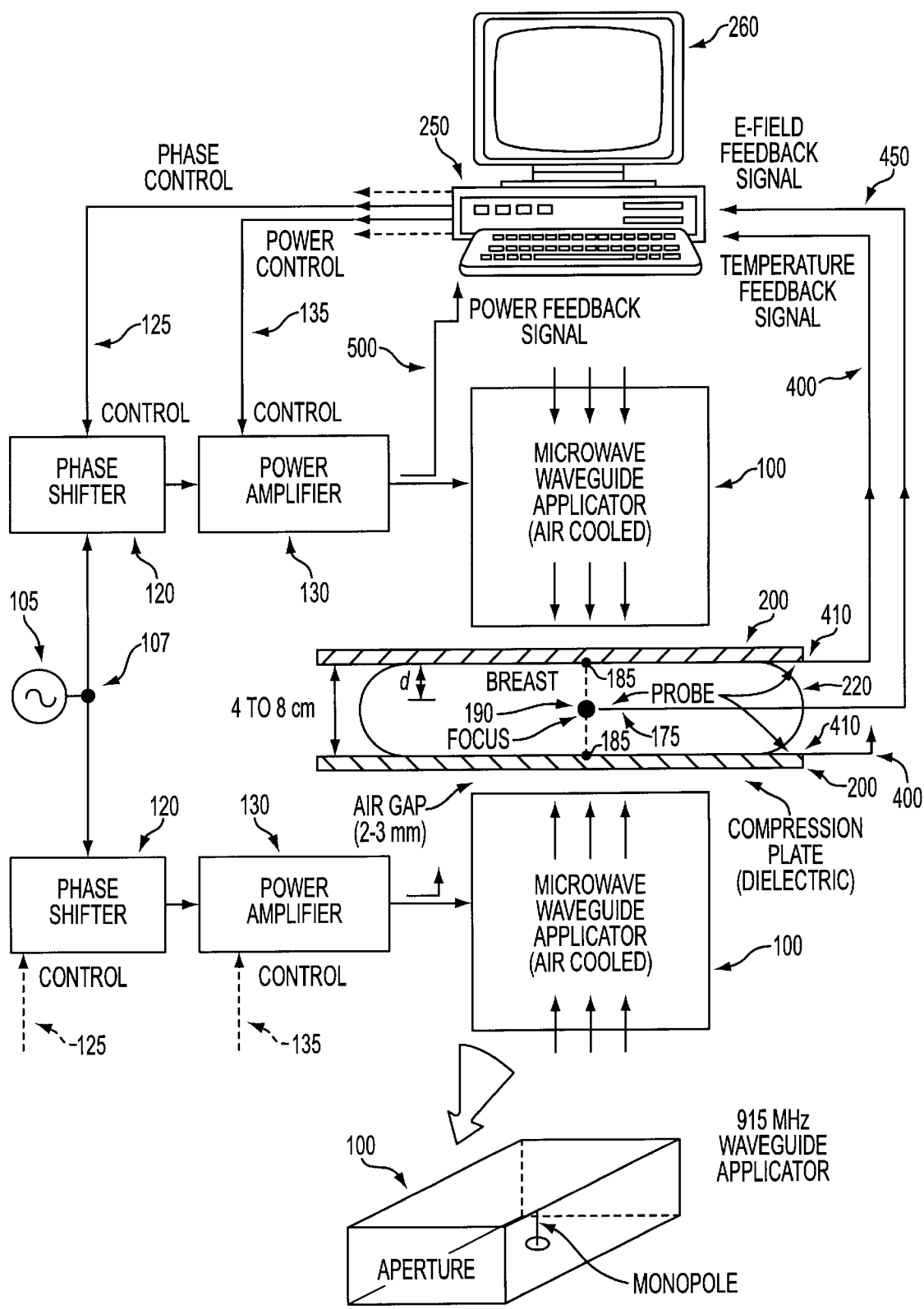
FIG. 5 shows the system according to the invention for heating the breast under compression.

Method for Heating Ductal and Glandular Carcinomas and Surrounding Breast Tissues FIG. 5 shows a preferred system for heating carcinomas in intact breast, using an adaptive microwave phased array hyperthermia system with E-field and temperature feedback. In order to heat deep tissues reliably at microwave frequencies, it is necessary to surround the body (breast) with two or more coherent applicators 100 controlled by an adaptive phased array algorithm. The black circle, indicated as focus 190, represents a tumor or healthy tissue that is to be treated. In the preferred embodiment, an E-field feedback probe 175 is used to focus the microwave radiation, and temperature feedback sensors 410 attached to the breast surface skin are used to adjust the microwave power level to heat the tumor to a desired temperature. A two-channel adaptive phased array is used to heat deep tissues within a compressed breast similar to the geometry used in x-ray mammography. Preferably, the E-field probe is used with an adaptive phased array fast-acceleration gradient search algorithm, as disclosed in U.S. Pat. No. 5,810,888 to Fenn, to target the microwave radiation at the tumor site.

Additionally, air-cooled waveguide applicator apertures preferably are used to provide a heating pattern that can heat large volumes of breast tissue containing ductal and glandular carcinomas. The air for cooling the waveguide apertures can be refrigerated, air-conditioned or room temperature. Based on the dielectric parameter differences at 915 MHz between high-water content tissues and normal breast tissue, the high-water content ductal and glandular carcinoma tissues and other lesions are expected to heat more rapidly than normal breast tissue. Thus, the treated region will be concentrated on the high-water content (cancerous and pre-cancerous) carcinoma tissue and benign lesions such as fibroadenomas and cysts, while sparing the normal (healthy) breast tissue.

The body or breast is compressed between two compression plates 200, which are made from a dielectric such as plexiglass that is transparent to microwaves. Breast compression has a number of potential advantages for intact breast hyperthermia treatments. Utilization of breast compression results in less penetration depth required to achieve deep microwave heating and reduces blood flow which also improves the ability to heat tissue. Injection of a local anesthetic drug such as lidocaine with ephinephrine or anti-angiogenesis drug into the breast tissue can be used to reduce local blood flow as well. Compressing the breast to a flat surface improves the interface and electric-field coupling between the microwave applicator and the breast tissue, and allows a single pair of applicators to treat a wide mange of breast sizes. Cooling of the breast compression plates with air during hyperthermia treatments helps avoid the potential for skin-surface hot spots. Compressing the breast with the patient in a prone position, such as that used in 20 to 40 minute stereotactic needle breast biopsyprocedures (Bassett et al., A Cancer Journal for Clinicians, Vol. 47, pp. 171–190, 1997), maximizes the amount of breast tissue within the compression device. Mild compression immobilizes the breast tissue such that any potential patient motion complications are eliminated. The compression plates 200, which can include small apertures, is compatible with x-ray and ultrasound imaging techniques to accurately locate the central glandular/ductal region and assist in the placement of the invasive E-field probe sensor. The amount of compression can be varied from about 4 to 8 cm to accommodate patient tolerance during a 20 to 40 minute or longer hyperthermia treatment. A patient-comfort study of breast compression in mammography indicated that mammography was painful (defined as either very uncomfortable or intolerable) in only 8% of the 560 women examined. In that study the mean compression thickness was 4.63 cm with a standard deviation (1 sigma) of 1.28 cm (Sullivan et al., Radiology, Vol. 181, pp. 355–357, 1991). Thus, hyperthermia treatments under mild breast compression for 20 to 40 minutes or longer is feasible.

Prior to hyperthermia treatment, the breast is compressed between compression plates 200 and a single invasive E-field feedback sensor 175 is inserted within the central glandular/ductal/tumor tissue site (focus 190) in the breast, parallel to the polarization of the microwave applicators 100. E-field probe 175 is used in monitoring the focal E-field amplitude as the phase shifters are adjusted for maximum feedback signal using an adaptive phased array gradient search algorithm. Noninvasive temperature probes 410 are taped or otherwise secured to the skin surface of the breast to monitor the skin temperature. The temperature probes are typically oriented at right angles to the E-field polarization so as not to be heated by the microwave energy. The dual-applicator adaptive phased array of the invention together with the E-field feedback probe allows the phase shifters to be adjusted so that a concentrated E-field can be generated permitting focused heating in tissue at depth.

Figure 6:
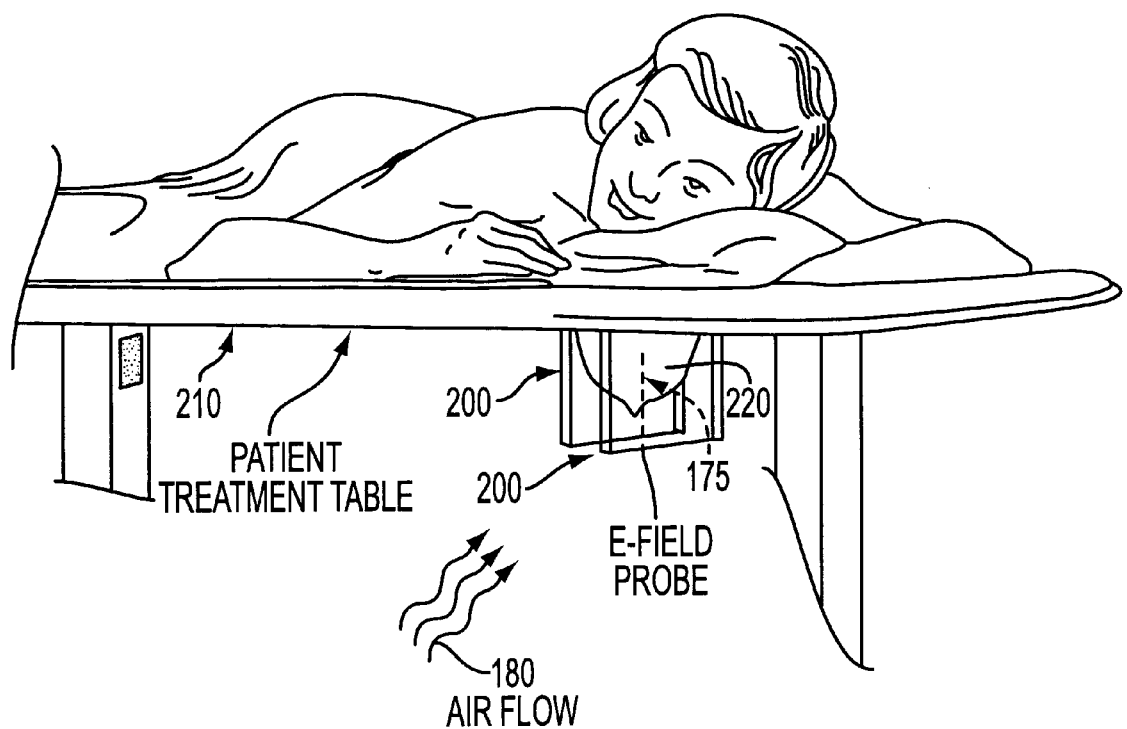
FIG. 6 shows the patient in a prone position with the breast compressed and an E-field probe inserted at the desired focal depth in the breast.

Referring to FIG. 6, in the preferred embodiment the patient lies prone with the breast pendulant through a hole in the treatment table 210 and the treated breast 220 is compressed with flat plastic compression plates 200 which immobilizes the breast tissue, reduces blood flow, and reduces the penetration depth required for the microwave radiation. The breast compression plates are made of a microwave transparent plastic material, and may contain one or more apertures of rectangular or circular shape to allow imaging of breast tissues and placement of a minimally invasive E-field feedback probe 175 at the desired focal depth. Insertion of E-field feedback probe 175 may be achieved under the guidance of an ultrasound transducer. To provide additional protection against skin damage from the microwave fields, air flow 180 is provided by one or more cool-air fans (not shown).

As shown in FIG. 5, two or more temperature feedback probe sensors 410 are attached to the breast skin surface and produce the temperature feedback signals 400. Two microwave air-cooled waveguide applicators 100 are positioned on opposite sides of the compression plates 200. A 915 MHz microwave oscillator 105 is divided at node 107 and feeds phase shifters 120. The phase control signal 125 controls the phase of the microwave signal over the range of 0 to 360 electrical degrees. The microwave signal from phase shifter 120 feeds into the microwave power amplifier 130 which is controlled by a computer-generated control signal 135, which sets the initial microwave power level. Coherent 915 MHz microwave power is delivered to the two waveguide applicators 100 while phase shifters 120 in each channel are adjusted to maximize and focus the microwave energy at the E-field probe sensor 175 so that microwave power is maximized at the focus position 190. The treatment then begins.

During the hyperthermia treatment, the microwave power level delivered to each of the applicators 100 is measured as a feedback signal 500, and the power control is adjusted either manually or automatically to control the skin temperatures and equivalent thermal dose measured by the skin sensors 410 to avoid high temperatures that could cause skin burns or blisters. The amount of breast compression is adjusted by the compression plates 200 as necessary during treatment to provide patient comfort. Each time the breast compression is adjusted or the breast repositioned, the phase shifters 120 are readjusted/refocused so that the E-field probe sensor 175 receives maximum power. The total microwave energy, since the start of the treatment, delivered to the microwave applicators is computed within the computer 250 and displayed on the computer monitor 260 during the treatment. The treatment is completed when a desired amount of total microwave energy is delivered to the microwave applicators 100. As an alternate embodiment, the total microwave energy calculated from the E-field feedback signal 450 received by the E-field probe 175 is used to control the length of the treatment. In order to determine the effectiveness of the treatment, the breast tissue is imaged with mammography means including x-ray and magnetic resonance imaging before and after the microwave total energy dose is administered, as well as pathological results from needle biopsy of the breast tissues.

As an alternate embodiment, the single invasive E-field probe 175 is replaced with two noninvasive E-field probes 185 positioned on the opposing skin surfaces. The total power measured by the two noninvasive E-field probes is minimized (as in U.S. Pat. No. 5,810,888) by adjusting the microwave phase shifters 120, creating a focused E-field in the central portion of the breast. With this embodiment, there is no risk of infection due to an inserted probe, there is no risk of scarring of the breast skin by the procedure of nicking the skin and inserting the probe, and any risk of spreading cancer cells by the probe passing through the tumor bed is avoided. Likewise, since both the temperature and E-field probes can be placed on the breast skin with this method embodiment, this method would work well when there is no defined single area.

Preferably, each channel (on either side of node 107) of the phased array contains an electronically-variable microwave power amplifier 130 (0 to 100 W), an electronically-variable phase shifter 120 (0 to 360 degrees), and aircooled linearly-polarized rectangular waveguide applicators 100. Applicators 100 may be Model Number TEM-2 manufactured by Celsion Corporation, Columbia, Md. The rectangular aperture dimensions of a preferred pair of TEM-2 metallic waveguide applicators are 6.5 cm by 13.0 cm.

While the preferred embodiment discloses microwave energy at approximately 915 MHz, the frequency of the microwave energy may be between 100 MHz and 10 GHz. The frequency of the microwave energy could be selected from the range of 902 MHz and 928 MHz. In fact, lower frequencies of energy may be used to ablate or prevent cancerous tissue.

In a preferred embodiment, the initial microwave power delivered to each waveguide applicator is between 20 and 60 Watts. Over the entire treatment of the tissue the microwave power delivered to each waveguide applicator. may be adjusted over the range of 0–150 Watts to deliver the desired microwave energy dose and to avoid overheating the skin.

Dielectric loading of the side walls of the rectangular waveguide region of applicators 100 is used to obtain good impedance matching conditions for the TEM applicator microwave radiation (Cheung et al., Radio Science, Vol. 12, No. 6(S) Supplement, pp 81–85, 1977; Gauthexie (Editor), Methods of external hyperthermic heating, Springer-Verlag, New Yozk, p. 33, 1990). Air cooling through the waveguide aperture is achieved by means of a fan (not shown) mounted behind a perforated conducting screen which serves as a parallel reflecting ground plane for the input monopole feed for the waveguide. Taking into account the thickness of the dielectric slabs in contact with the waveguide side walls, the effective cross-sectional size for the air cooling is approximately 6.5 cm by 9.0 cm for the TEM-2 applicator. Based on the dielectric parameter differences at 915 MHz between high-water content tumor tissues and normal breast tissue, the high-water content ductal and glandular carcinomas and benign lesions are expected to heat more rapidly than normal breast tissue. Thus, the 50% SAR region will be concentrated on the high-water content (cancerous, pre-cancerous, and benign lesions including fibroadenomas and cysts) tissue while sparing the normal tissue.

In a preferred embodiment, a 0.9-mm outside-diameter (OD) invasive E-field coaxial monopole probe (semi-rigid RG-034), with the center conductor extended 1 cm, can be used to measure the amplitude of the electric field directed to the tissue and provide the feedback signal used to determine the necessary relative phase for the electronic phase shifters prior to treatment. Coaxially-fed monopole probes of this type have been used to make accurate measurements of linearly polarized electric fields in compressed breast phantoms (Fenn et al., International Symposium on Electromagnetic Compatibility May 17–19, 1994 pp. 566–569) Journal of Hyperthermia, Vol. 10, No. 2, March–April, pp. 189–208, 1994). This linearly-polarized E-field probe is inserted within a 1.5 mm OD teflon catheter. Thermocouple probes (Physitemp Instruments, Inc., Type T copper-constantan, enclosed within a 0.6 mm OD teflon catheter) were used to measure the local temperature in the tumor during treatment. These temperature probes have a response time of 100 ms with an accuracy of 0.1° C.

Compressed Living Breast Tissue Heating Tests

As part of an FDA-approved Phase I clinical study conducted by the assignee, Celsion Corporation, beginning in December 1999, several volunteer patients, with breast tumors varying in maximum dimension from 3 to 6 cm, were treated with an adaptive microwave phased array where both E-field and temperature probes were inserted into the breast tissue. Patients received a 40-minute treatment of hyperthermia and approximately one-week later underwent mastectomy. This clinical study included a measurement of the power delivered to the microwave applicators, which was used to compute the delivered microwave energy dose, but was not used to control the duration of the treatment.

The E-field probe was used with the adaptive phased array fast-acceleration gradient search algorithm, as disclosed in U.S. Pat. No. 5,810,888 to Fenn, to target the microwave radiation at the tumor site. The temperature sensed by the invasive temperature probe in the tumor was used as a real-time feedback signal during the treatment. This feedback signal was used to control the microwave output power level of the variable power amplifiers, which set and maintained the focal temperature at the tumor site in the range of 43 to 46° C. The power and phase delivered to the two channels of the phased array were adjusted adaptively using digital-to-analog converters under computer control.

The breast compression plates were made of an acrylic material (plexiglass) which is a low-loss dielectric material and nearly transparent to microwave fields. The compression plates contained square cut-outs (apertures), approximately 5.5 cm on a side, which accommodate small ultrasound transducers (nominally 4 cm in length) to assist in placement of the minimally invasive probes (E-field and temperature). The cut-outs also allow improved air flow to cool the skin.

Based upon the results from these recent microwave hyperthermia clinical tests with adaptive microwave phased array treatment, Applicants recognized, in living breast tissue compressed to 4.5 to 6.5 cm, that a microwave energy dose of between 138 kJ (kilojoules or equivalently kW seconds) and 192 kJ produces an equivalent thermal dose ranging from 24.5 minutes to 67.1 minutes relative to 43° C. as listed below in Table 1.

TABLE 1

Equivalent thermal dose (minutes) and total microwave energy (kilo-Joules) delivered in the four compressed living breast tissue tests.

|  | $T_{43°\ C.}$ equivalent thermal dose measured in tumor (minutes) | Total Microwave Energy Dose (kJoules) |
|---|---|---|
| Test 1 | 41.0 | 192.0 |
| Test 2 | 24.5 | 162.0 |
| Test 3 | 67.1 | 186.0 |
| Test 4 | 47.8 | 138.0 |
| Average | 45.1 | 169.5 |

Thus, the Total Microwave Energy Dose can be used to estimate the required heating time. That is, Applicants realized that a non-invasive equivalent temperature sensing means could replace the invasive temperature probes, and that the Total Microwave Energy Dose reliably could be used to control the duration of treatment. In Table 1, the average thermal dose is 45.1 minutes and the average Total Microwave Energy is 169.5 kJ. In these four tests, the maximum energy value (192.0 kJ) varies by only 13% from the average and the minimum energy value (138.0 kJ) varies by only 14% from the average. The breast compression used in these tests, as mentioned earlier, reduces blood flow which likely eliminates the effects of blood flow on the required microwave energy for treatment, and may help explain the small variation in energy required in these tests. Applicants also recognized that post treatment imaging of these four tests typically showed significant damage to the tumor, but little or no damage to the skin, breast fat, and normal glandular, ductal, and connective tissues.

Accordingly to a preferred embodiment of the method, the total microwave energy delivered to the waveguide applicators to determine completion of the treatment is between 25 kilojoules and 250 kilojoules. The total amount of microwave energy dose that would destroy any cancerous or precancerous tissue would be approximately 175 kilojoules. But, under certain conditions, the required microwave energy dose may be as low as 25 kilojoules.

Table 2 below lists the breast tissue compression thickness for the four tests. It should be noted that the smallest compression thickness (4.5 cm) corresponds to the smallest energy dose (138 kJ) delivered, with both occurring in Test 4. As applicants recognized and will be proven theoretically below, smaller compression thickness may require less microwave energy dose (compared to larger compression thickness) for effective treatments in preventing or destroying cancerous, pre-cancerous or benign lesions.

TABLE 2

Breast compression thickness for the four compressed living breast tissue tests.

|  | Breast Compression Thickness (cm) |
|---|---|
| Test 1 | 6.5 |
| Test 2 | 6.5 |
| Test 3 | 6 |
| Test 4 | 4.5 |

From these clinical studies, it becomes apparent that it is important to select an appropriate initial microwave power level ($P_1, P_2$) delivered to each applicator as well as the proper microwave phase between the two applicators to focus the energy at the area to be treated. From the compressed breast experiments, the following data was obtained for the four tests as listed in Table 3:

TABLE 3

Initial microwave power and initial microwave phase to focus the radiation in compressed living breast tissue.

|  | Initial Microwave Powers $P_1, P_2$ (W) | Relative Microwave Phase (deg) |
|---|---|---|
| Test 1 | 30 | −90 |
| Test 2 | 30 | −180 |
| Test 3 | 40 | −180 |
| Test 4 | 40 | −10 |

As can be seen from Tables 1 and 3, initial microwave power of 30 to 40 watts for each applicator was sufficient to achieve significant thermal doses. Further, the initial relative microwave phase between the applicators varied from −10 electrical degrees to −180 electrical degrees and does not follow any definite trend, proving that it is necessary to always focus the microwave radiation with an E-field sensor.

For comparable compression thickness, 6.5 and 6.0 cm in Tests 2 and 3, respectively, the microwave power level was held constant for the first few minutes of the treatments in order to determine the linear temperature rise in the tumor—this in effect provides a measurement of the SAR. It was found for 30 watts of power, that it took 2.5 minutes to achieve a one-degree C temperature rise in the tumor. For 40 watts of power, it took only 1.5 minutes to achieve a one-degree C temperature rise.

During hyperthermia treatment, it is necessary to monitor the skin temperatures so that they do not rise significantly above about 41 degrees Celsius for more than several minutes. The equivalent thermal dose for the skin can be calculated (Sapareto, et al., International Journal of Radiation Oncology Biology Physics, Vol. 10, pp. 787–800, 1984) and can be used as a feedback signal. Typically, it is necessary to avoid delivering more than a few equivalent minutes thermal dose. Avoiding high skin temperatures according to the invention is accomplished by adjusting the individual powers ($P_1$, $P_2$) delivered to the applicators during treatment either by manual or automatic computer control.

Applicants recognize that Doppler ultrasound can be used to measure blood flow in tumors and surrounding breast tissue, before and during treatment to plan and adjust the microwave energy dose. For example, less energy dose is required when the tumor blood flow rate is reduced which can occur when the breast is compressed and/or the tumor is heated to therapeutic temperatures. Alternatively, the water content and dielectric parameters of breast tumor tissue from needle biopsies could be measured and used to determine, prior to the treatment, the required microwave energy dose. For example, higher water content and higher electrical conductivity in the tumor would reduce the amount of required microwave energy dose. In addition to the above variables, the size of the tumor impacts the required microwave energy dose. Larger tumors are more difficult to heat than smaller tumors and require a larger microwave energy dose. An initial treatment planning session involving a low-dose delivery of microwave energy to assess the heatability of the tumor, followed by a complete treatment at the full required microwave energy dose may be performed.

Simplified Microwave Radiation Theory

Microwave energy from hyperthermia applicators, in the near field of a body, radiates as a spherical wave with the electric-field amplitude varying, in part, as the inverse of the radial distance r from the applicator. Additionally, the amplitude decays as an exponential function of the product of the attenuation constant a of the body tissue and the distance d traversed (or depth) within the body. The electric-field phase varies linearly with distance according to the product of the phase propagation constant $\Delta$ and distance d. For simplicity, dual-opposing applicators are analyzed here under the assumption that the applicator radiation is approximated by a plane wave. Mathematically, the plane-wave electric field versus depth in tissue is given by $E(d)=E_o \exp(-\alpha d) \exp(-\beta d)$, where $E_o$ is the surface electric field (in general represented by an amplitude and phase angle), i is the imaginary number (Field and Hand, An Introduction to the Practical Aspects of Clinical Hyperthermia, Taylor & Francis, New York p. 263, 1990).

Plane-wave electromagnetic energy, at the microwave frequency of 915 MHz, attenuates at a rate of about 3 dB per cm in high-water content tissue, such as ductal or glandular breast tumor, and about 1 dB per cm in normal breast tissue. Thus, a single radiating applicator has a significant fraction of its microwave energy absorbed by intervening superficial body tissue compared to the energy that irradiates deep tissue, likely creating a hot spot in superficial tissue. Since skin surface cooling with either air or water protects tissue only to a maximum depth of about 0.25 to 0.5 cm, in order to avoid hot spots, it is necessary to introduce a second phase-coherent applicator, having the same microwave radiation amplitude as the first applicator. The second phase-coherent applicator can theoretically increase the power (and hence the energy) delivered to deep tissue by a factor of four compared to a single applicator (Field and Hand, p. 290, 1990).

The phase characteristics of the electromagnetic radiation from two or more applicators (known as a phased array) can have a pronounced affect on the distribution of power delivered to different tissues. The relative specific absorption rate (SAR) in homogeneous tissue is approximated by the square of the electric-field amplitude $|E|^2$. The SAR is proportional to the rise in temperature over a given time interval. A simplified case, homogeneous breast tissue, in which the microwave radiation is focused at a central tissue site is described in detail below. As described in an article by Fen et al., International Symposium on Electromagnetic Compatibility, Sendai, Japan, Vol. 10, No. 2, May 17–19, 1994, pp. 566–569, the effects of multiple microwave signal reflections within the breast phantom can be ignored.

The wavelength in homogeneous normal breast tissue (with approximate dielectric constant 12.5 and electrical conductivity 0.21 S/m (values averaged from Chaudhary et al., 1984, Joines et al., 1994) is approximately 9.0 cm at 915 MHz, and the microwave loss is (1 dB(cm). The attenuation constant $\alpha$ is 0.11 radians/cm and the propagation constant $\beta$ is 0.69 radians/cm. (For a phantom thickness of 4.5 cm, the electric field of a single applicator radiating on the left side is $E_o$ at the surface, $-i0.8E_o$. (where i represents a 90-degree phase shift) at the central position (2.25 cm deep), and $-0.6E_o$ at the right surface. Combining two phase coherent applicators yields an electric-field value of $0.4E_o$ on both surfaces and $-i1.6E_o$ at the central position (2.25 cm depth). Thus, for breast that there is a significantly lower SAR at the surface, by a factor of 16 compared to the central SAR. The 180-degree phase shift experienced by the microwave field transmitted through 4.5 cm of breast tissue, partly cancels or nulls the field entering the tissue with 0-degree phase shift. Due to destructive interference of the microwaves away from the central focus lower temperatures in the superficial breast tissues would be expected. Measurement and enforcement of lower SAR on the opposing skin surfaces effectively focuses the microwave energy deep in the breast.

The adaptive phased array system according to the invention uses two microwave channels, fed by a common oscillator 105, containing two electronically adjustable phase shifters 120 to focus the microwave energy at an E-field feedback probe 175. This inventive adaptive phased array system has significant advantage over a non-adaptive phased array. A non-adaptive phased array with two channels could, in theory, produce a null, a maximum, or an intermediate value of E-field depending on whether the two waves are 180 degrees out-of-phase, completely in-phase, or partly out-of-phase, respectively. That is, the microwave phase delivered to the microwave applicators, according to the invention, can be adjusted between −180 degrees and 180 degrees before and during the treatment to create a focused field in the breast tissue.

Because the adaptive phased array according to the invention automatically focuses the E-field in the presence of all scattering structures in the tissue, this type of array should provide more reliable deep focused heating compared to manually adjusted or pre-treatment planning controlled phased arrays as described in U.S. Pat. No. 4,589,423 to Turner. Furthermore, the adaptive phased array system according to the invention does not use an invasive temperature probe which could scatter or alter the E-field at the tumor site.

Calculation of Microwave Energy

Electrical energy consumption is commonly expressed in units of kilowatt hours. Mathematically, the expression for the microwave energy W delivered by an applicator is given by (Vitrogan, Elements of Electric and Magnetic Circuits, Rinehart Press, San Francisco, pp. 31–34, 1971):

$$W = \Delta t \Sigma P_i \quad (1)$$

In the above equation, Δt represents the constant intervals (in seconds) in which microwave power is measured and the summation Σ is over the complete treatment interval with the power (in Watts) in the with interval denoted by $P_i$.

The microwave energy W has units of watt-seconds, which is also designated as Joules. For example, in three consecutive 60-second intervals if the microwave power is 30 watts, 50 watts, 60 watts, respectively, the total microwave energy delivered in 180 seconds is calculated as W=60 (30+50+60)=8,400 watt-seconds=8,400 Joules=8.4 kJ.

To understand better the focused energy per unit time W' (where ' denotes prime) deposited at a central position in homogeneous breast tissue of varying thickness (denoted by D) by dual-opposing applicators, consider the following calculation. Let $P_1$ and $P_2$ be the power delivered to the two applicators, respectively. The electric field radiated by each applicator is proportional to the square root of the power delivered to the applicator. Assuming symmetry, the radiated fields are in-phase at the central focused position from the two applicators. Assuming equal power from each applicator, that is, $P_1=P_2=P$, and plane wave illumination, then the focused energy per unit time at the central depth is expressed as $$W'(D)=|E|^2=4P\exp(-\alpha D). \quad (2)$$

Figure 7:
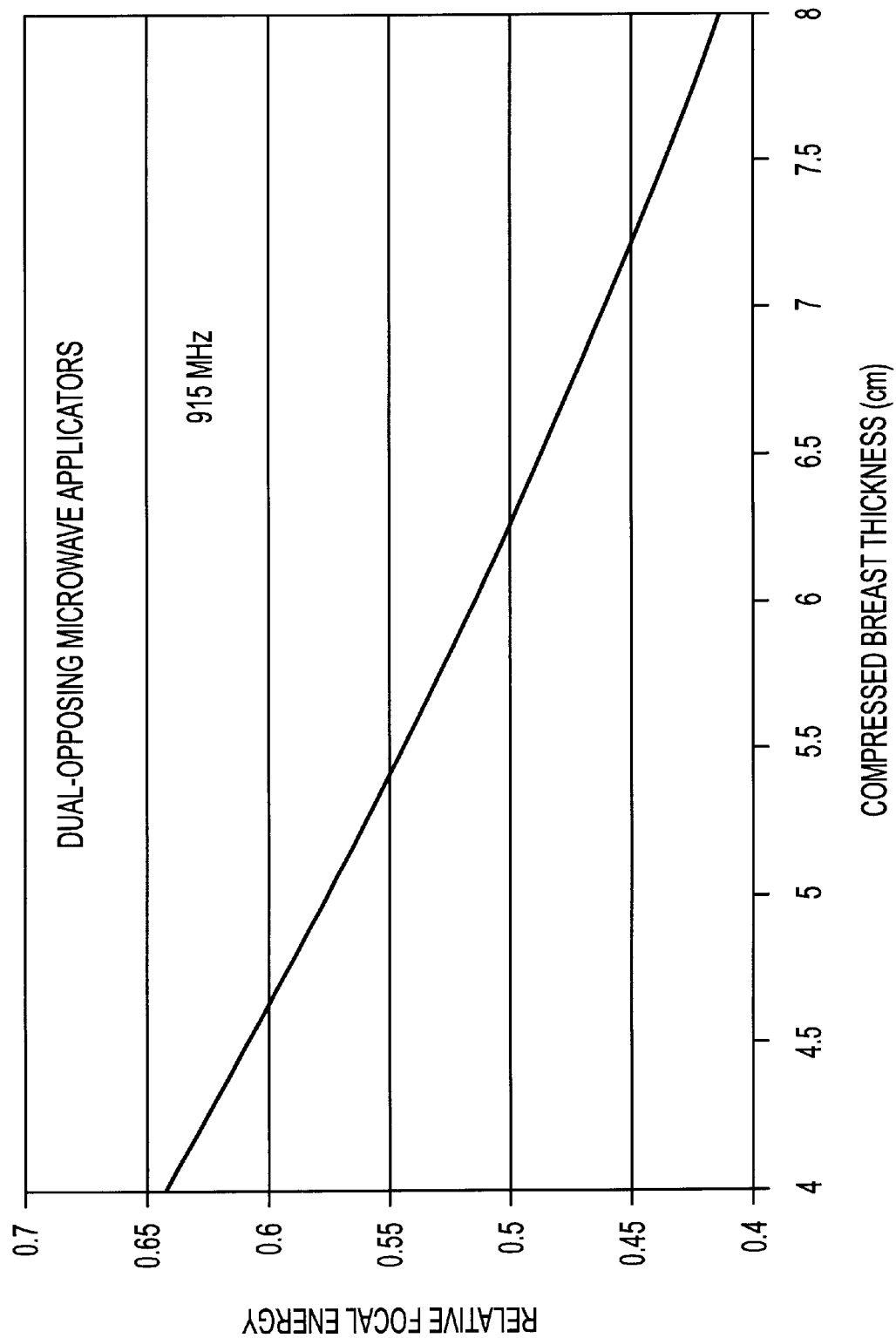
FIG. 7 shows the calculated focal microwave energy as a function of compressed breast tissue thickness.

Equation (2) was used to compute the focused 915 MHz energy per unit time at the central depth of normal breast tissue varying in thickness from 4 cm to 8 cm with the attenuation constant equal to 0.11 radians/cm, as shown in Table 4 and FIG. 7.

TABLE 4

Relative microwave energy at a central focus in simulated normal breast tissue for dual-opposing 915 MHz plane waves.

| Compression Thickness (cm) | Relative Energy at Focus |
|---|---|
| 4.00 | 0.643 |
| 4.25 | 0.626 |
| 4.50 | 0.608 |
| 4.75 | 0.592 |
| 5.00 | 0.576 |
| 5.25 | 0.560 |
| 5.50 | 0.545 |
| 5.75 | 0.530 |
| 6.00 | 0.516 |
| 6.25 | 0.502 |
| 6.50 | 0.488 |
| 6.75 | 0.475 |
| 7.00 | 0.462 |
| 7.25 | 0.449 |
| 7.50 | 0.437 |
| 7.75 | 0.425 |
| 8.00 | 0.413 |

It can be shown that for a given power level, higher energy occurs at the focus as the focal position moves towards the skin.

Calculation of Equivalent Thermal Dose

The cumulative or total equivalent thermal dose relative to 43 degrees Celsius is calculated as a summation (Sapareto, et al., International Journal of Radiation Oncology Biology Physics, Vol. 10, pp. 787–800, 1984):

$$t_{43°C}\text{equivalent minutes}=\Delta t\Sigma R^{(43-T)}, \quad (3)$$

where Σ is the summation over a series of temperature measurements during the treatment, T is the series of temperature measurements ($T_1, T_2, T_3, \ldots$), Δt is the constant interval of time (units of seconds and converted to minutes) between measurements, R is equal to 0.5 if T>43° C. and R is equal to 0.25 if T<43° C. The equivalent thermal dose calculation is useful for assessing any possible heat damage to the breast tissues and skin.

Detailed Microwave Specific Absorption Rate Calculations in Simulated Breast Tissue To estimate the heating pattern in normal breast tissue and in normal breast tissue with tumor exposed to microwave radiation, three-dimensional specific absorption rate (SAR) heating patterns were calculated using finite-difference time-domain theory and computer simulations (Taflove, Computational Electrodynamics: The finite-difference time-domain method, Artech House, Inc., Norwood, Mass. p. 642, 1995). As depicted in FIG. 7, these simulations were performed by modeling dual-opposing TEM-2 waveguide applicators (Celsion Corp., Columbia, Ma.) operating at 915 MHz. The applicators were coherently combined to focus the radiated beam at the central position in 6 cm thick homogeneous normal (mixture of fat and glandular) breast tissue. The applicators are assumed to radiate through thin sheets of plexiglass that simulate the plates used for breast compression in the adaptive phased array breast hyperthermia system.

Figure 8:
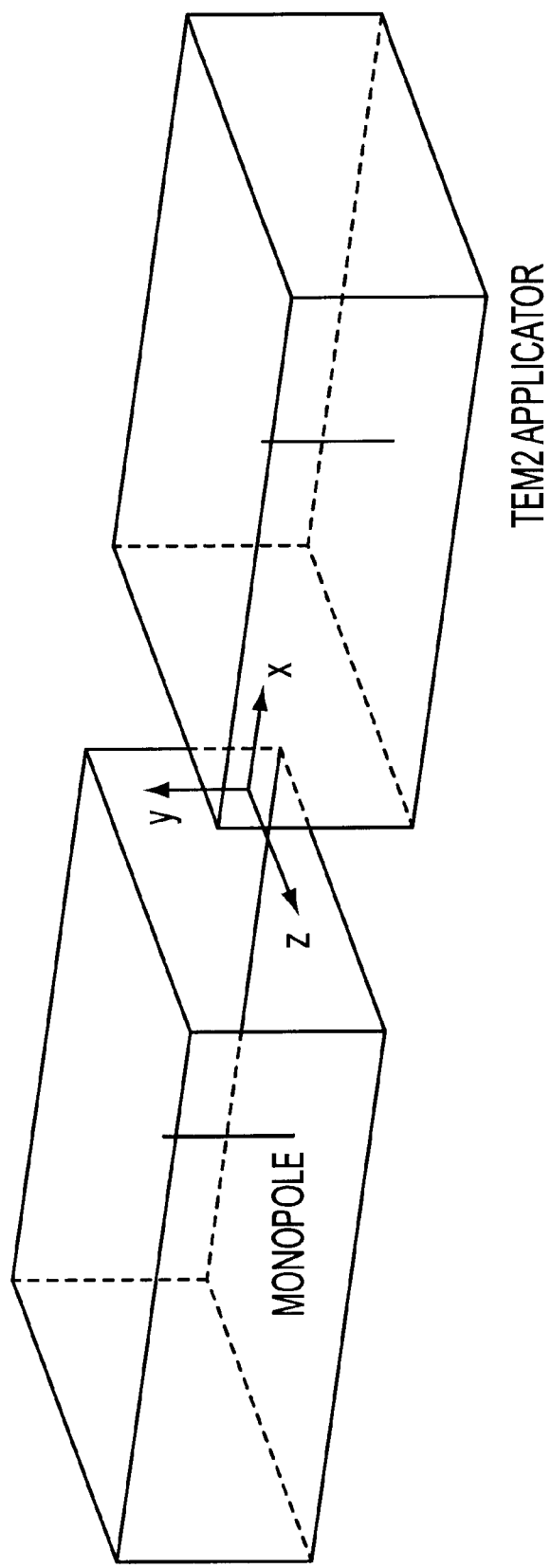
FIG. 8 shows a three-dimensional view of the computer simulated dual-opposing microwave waveguide applicators used in heating the breast.

Each metallic waveguide is loaded on the side walls with high dielectric constant material, which is used to match and shape the radiation inside the waveguide aperture. The waveguide applicators are linearly polarized with the alignment of the E-field in they direction as in FIG. 8. A flat sheet of 3 mm thick plexiglass is adjacent to each applicator and parallel to the waveguide aperture. Between the two opposing TEM-2 applicators is a 6 cm thick homogeneous normal breast tissue phantom. The remaining volume is filled with cubic cells that model air.

The SAR distributions were calculated by squaring the electric field amplitude and multiplying by the electrical conductivity of the tissue. SAR is often described in levels (50% is usually designated as the effective heating zone) relative to the maximum SAR value of 100%. The SAR is proportional to the initial rise in temperature per unit time ignoring blood flow and thermal conduction effects.

Figure 9:
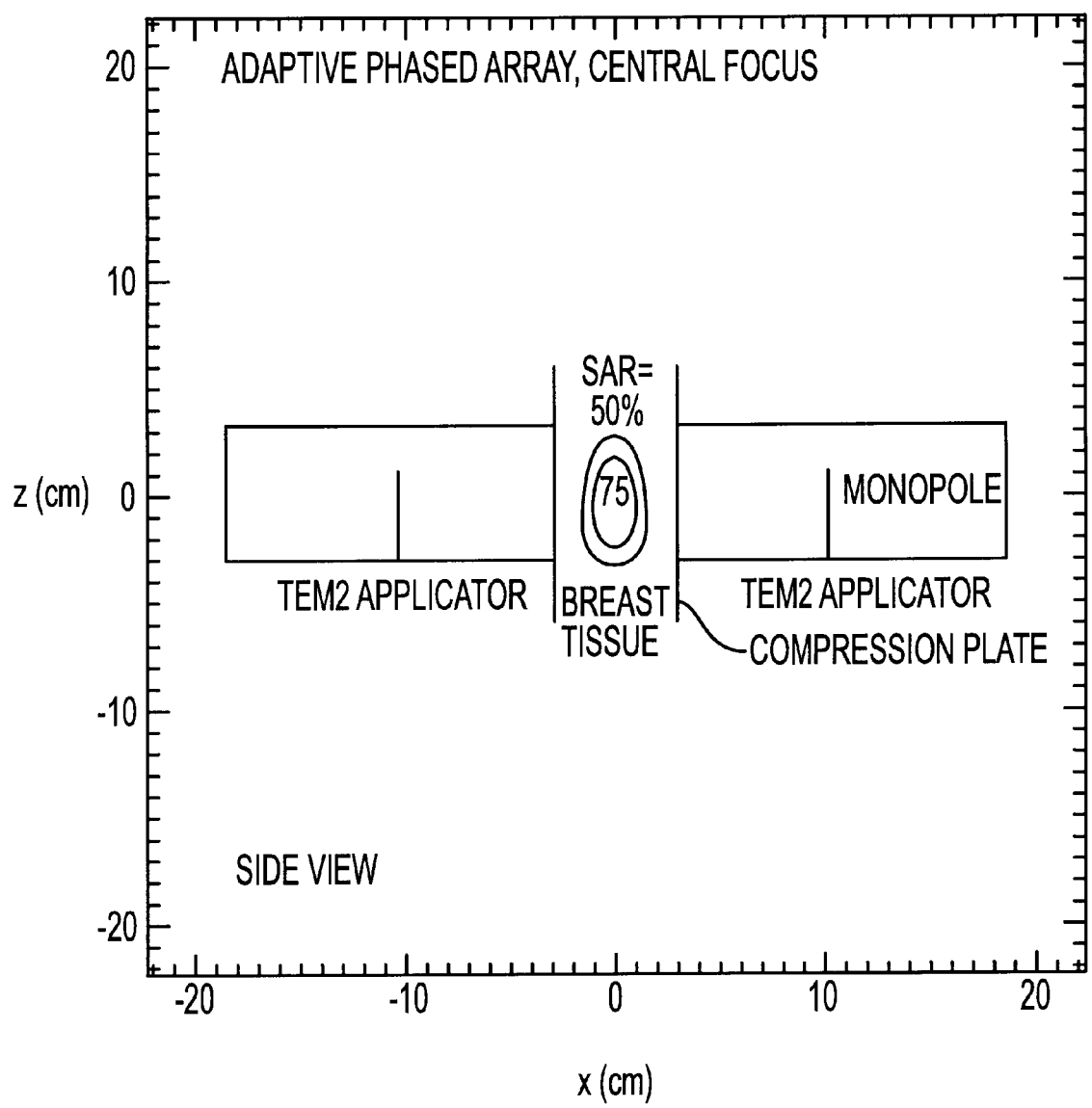
FIG. 9 shows a calculated side view of the 915 MHz specific absorption rate (SAR) heating pattern in homogeneous normal breast tissue with central focus.
Figure 10:
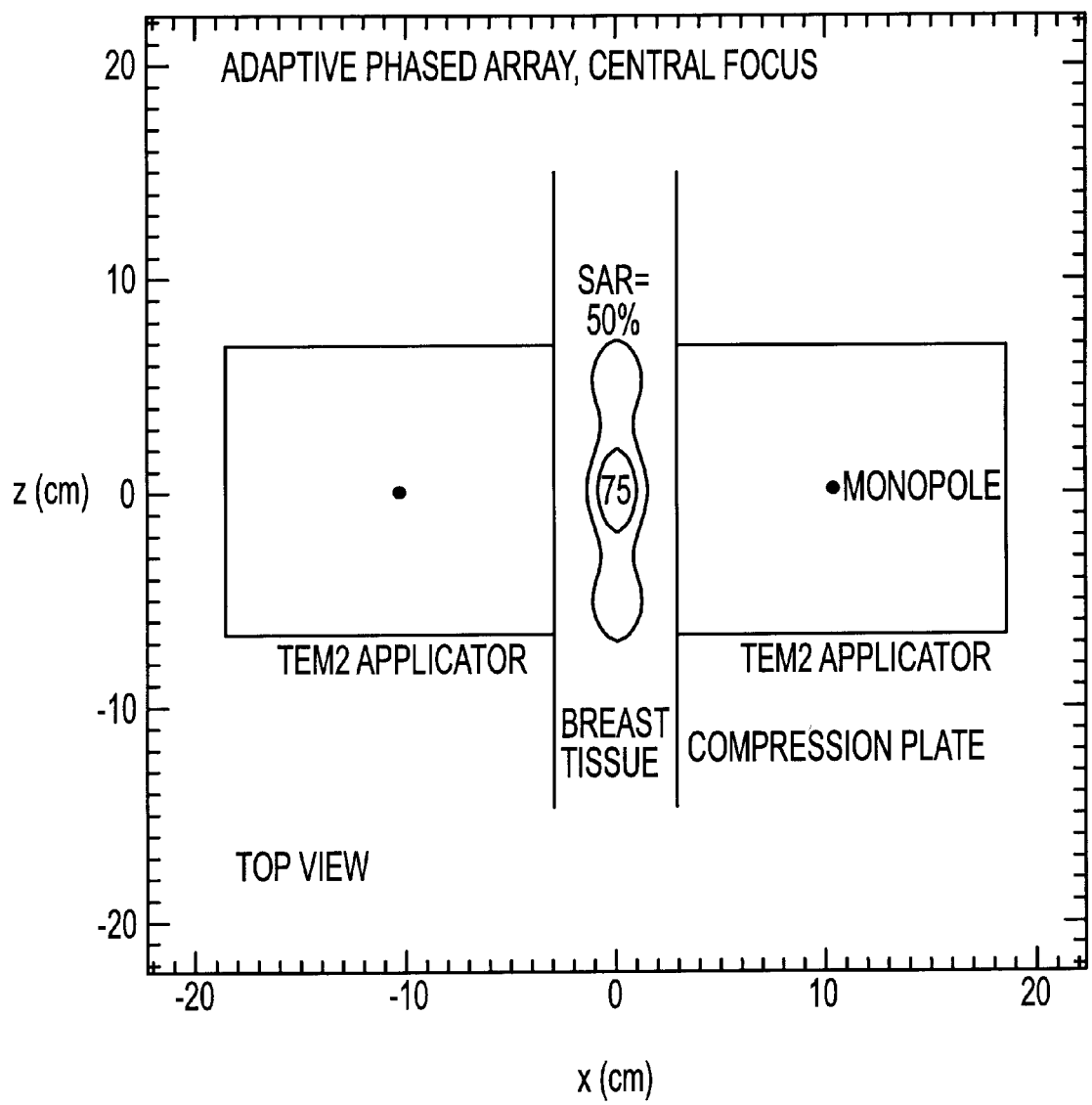
FIG. 10 shows a calculated top view of the 915 MHz SAR heating pattern in homogeneous normal breast tissue with central focus.
Figure 11:
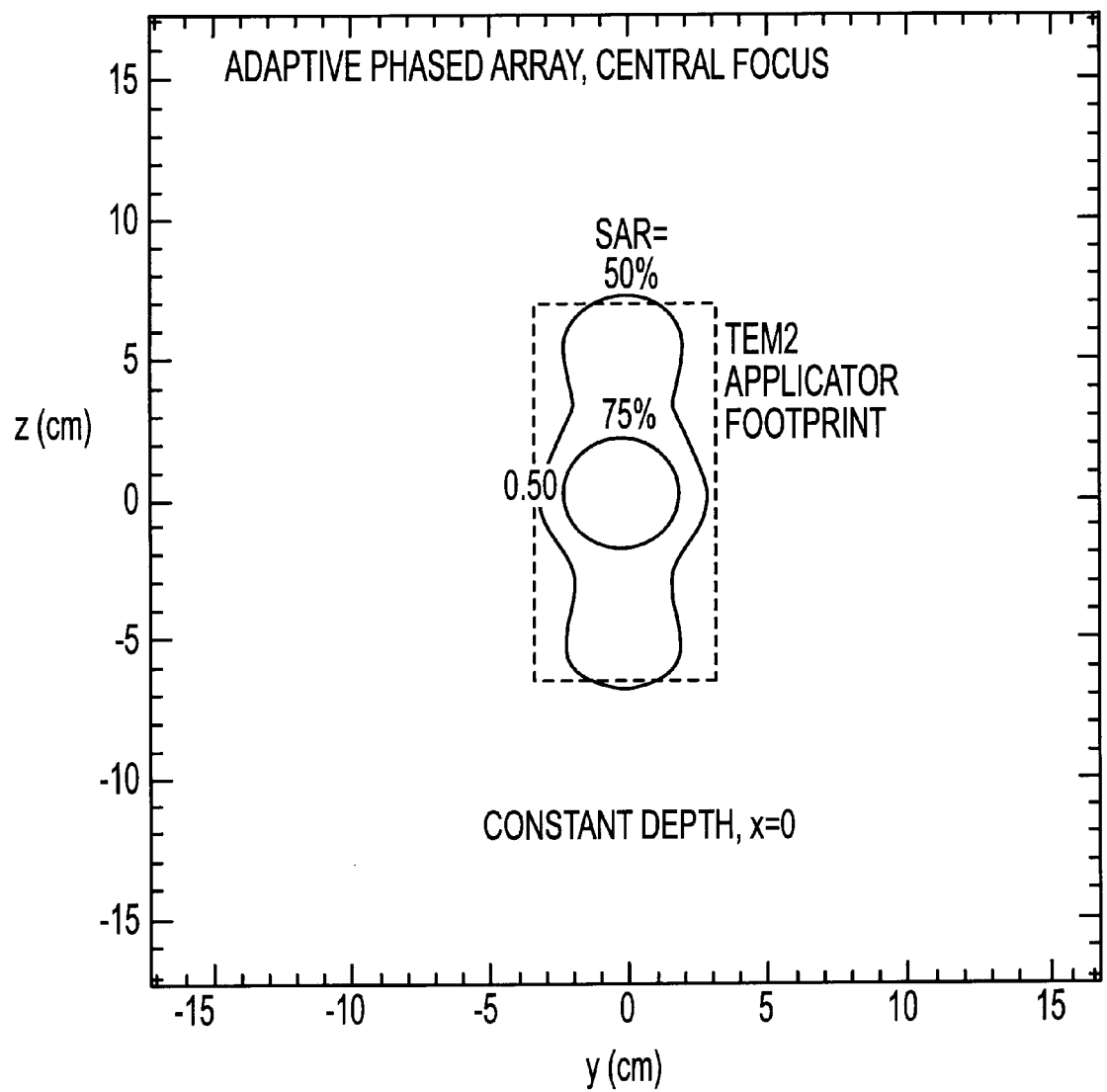
FIG. 11 shows a calculated end view of the 915 MHz SAR heating pattern in homogeneous normal breast tissue with central focus.

The SAR patterns were computed in the three principal planes (xy, xz, yz) as shown in FIGS. 9 to 13 for homogeneous normal breast tissue. The SAR side view (xy plane, z=0) pattern (75% and 50% contours) in homogenous normal breast tissue is shown in FIG. 9. The pattern generally is bell shaped and centered between the TEM-2 applicators. FIG. 10 shows the top view (xz plane, y=0) SAR pattern (75% and 50% contours). The pattern exhibits a small elliptically shaped 75% SAR region surrounded by a three-lobe shaped elliptical 50% SAR region. The small size of the 75% SAR is due to the mode shape of the radiated electric field for this type of applicator. FIG. 11 shows the end view (yz plane, x=0) of the SAR pattern (75% and 50% contours). The pattern exhibits a small circularly shaped 75% SAR region surrounded by a three-lobe shaped elliptical 50% SAR region approximately the size of the waveguide aperture.

The results shown in FIGS. 9 to 11 show that a large volume of deep breast tissues can be heated by the adaptive phased array with TEM-2 waveguide applicators, whereas the superficial tissues are not substantially heated. Any high-water content tissues exposed to this large heating field will be preferentially heated compared to the surrounding normal breast tissue. To demonstrate selective (preferential) heating, two spherically shaped 1.5-cm diameter simulated tumors (dielectric constant 58.6, electrical conductivity 1.05

Figure 12:
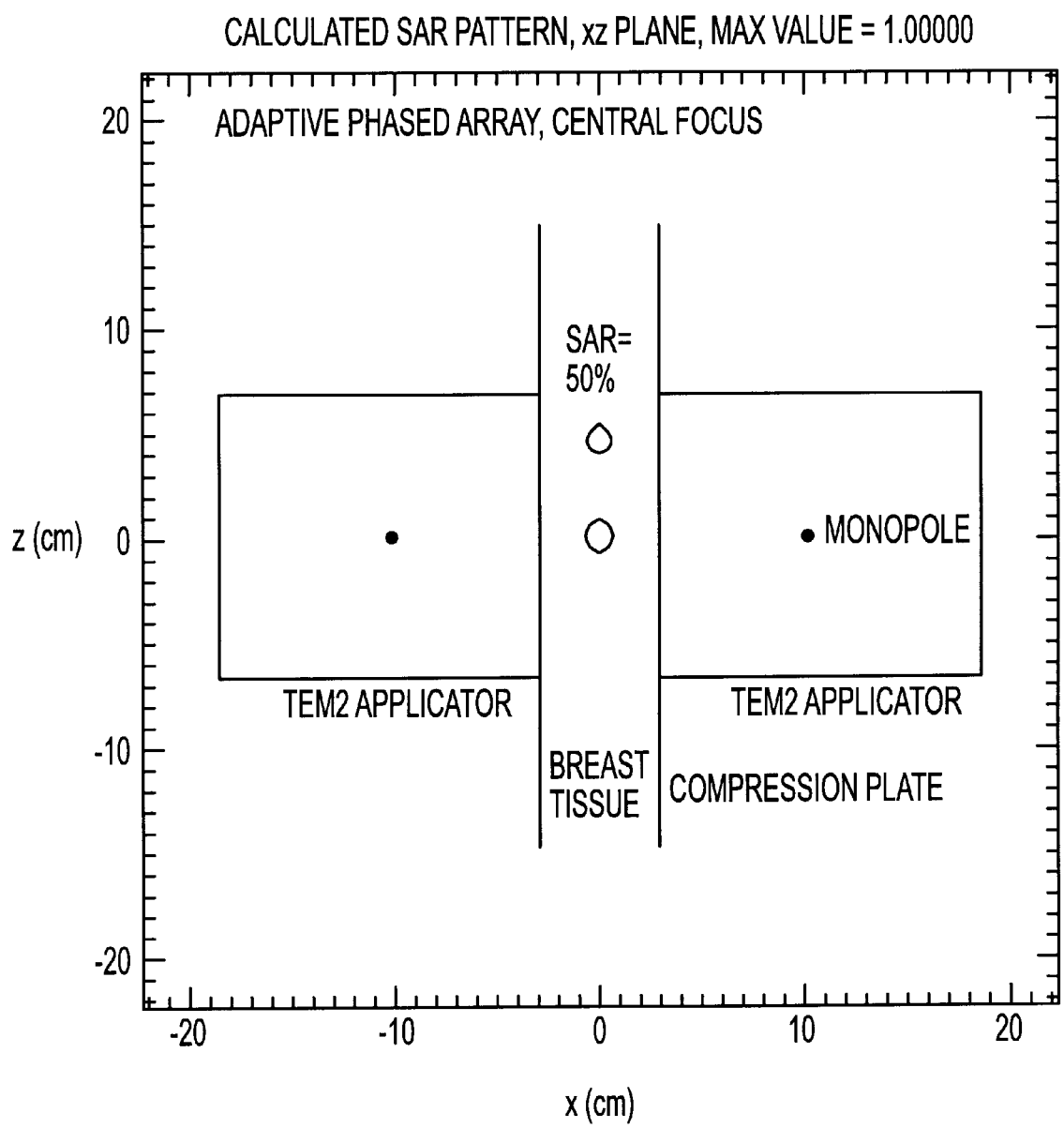
FIG. 12 shows a calculated top view of the 915 MHz SAR heating pattern when there are two simulated breast tumors, each with a diameter of 1.5 cm, spaced 5 cm apart The 50% SAR contours are aligned with the tumors indicative of selective heating.
Figure 13:
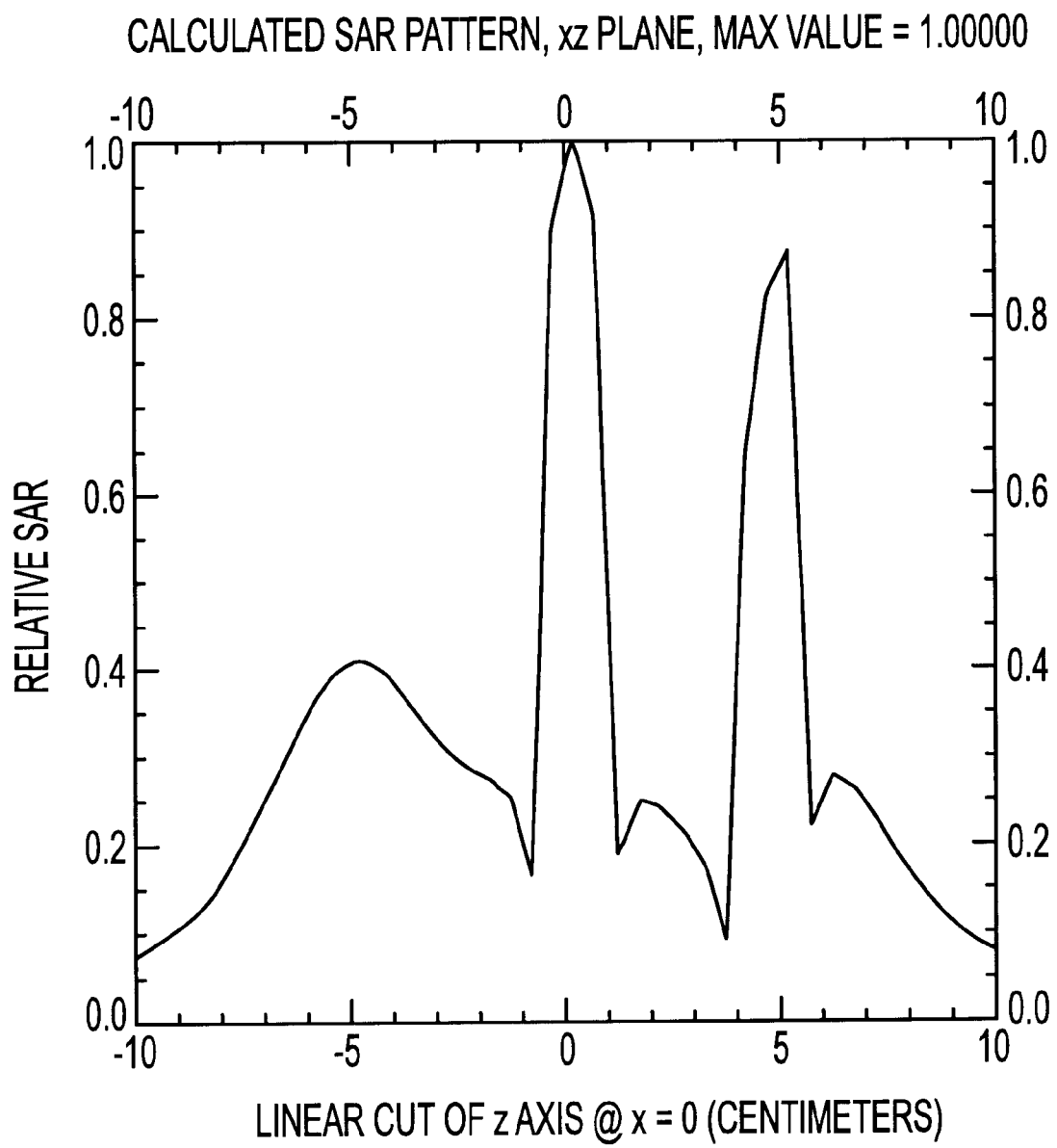
FIG. 13 shows a calculated linear cut of the 915 MHz SAR heating pattern (through the central plane of FIG. 12) when there are two simulated breast tumors, each with a diameter of 1.5 cm, spaced 5 cm apart. The SAR has sharp peaks that are aligned with the tumors indicative of selective heating.

S/m) were embedded in the normal breast tissue with 5-cm spacing and the FDTD calculation for the top view is shown in FIG. 12. Comparing this result with FIG. 10, it is clear that the SAR pattern has changed significantly and the two high-water content tumor regions are selectively heated. To show the sharpness of the selective heating the calculated SAR pattern along the z axis at x=0 cm is shown in FIG. 13. There is a sharp peak located at the positions of the two tumors, again demonstrating selective heating of high-water content carcinoma compared to the surrounding normal breast tissue. Similar results would be expected for benign breast lesions such as fibroadenomas and cysts.

While this invention has been particularly shown and described with reference to preferred embodiments thereof, it will be understood by those skilled in the art that various changes in form and details may be made therein without departing from the spirit and scope of the invention as defined by the appended claims. For instance, although the hyperthermia system described herein is with respect to the treatment of breast carcinomas and benign breast lesions, the invention is applicable to the treatment of other types of cancers such as prostate, liver, lung, and ovarian as well as benign disease such as benign prostatic hyperplasia (MPH). It is also understood that larger or smaller numbers of array antenna applicators, or single antenna applicators, may be used with similar results. Some of the methods and techniques described herein are also applicable to ultrasound hyperthermia system particularly the use of energy dose for feedback control. The method can be used to enhance radiation therapy or for targeted drug delivery and/or targeted gene therapy delivery using thermosensitive liposomes. The invention is also applicable to non-medical hyperthermia systems, such as those used for industrial heating.

We claim:

1. A method for treating cancerous or benign conditions of the breast by selective irradiation of the breast tissue with focused microwave energy, the method comprising the steps of:
   a) Inserting an E-field probe sensor to an appropriate depth in the breast tissue;
   b) Monitoring temperatures of the breast skin surface;
   c) Orienting two microwave applicators on opposite sides of the breast;
   d) Setting the initial microwave power delivered to each microwave applicator;
   e) Setting the initial relative microwave phase delivered to each microwave applicator to focus the microwave energy at the E-field probe positioned in the breast tissue;
   f) Adjusting the relative microwave power to be delivered to each microwave applicator during treatment based on the monitored skin temperatures;
   g) Monitoring the microwave energy delivered to the microwave applicators; and
   h) Completing the treatment when a desired total microwave energy dose has been delivered by the microwave applicators to the breast.

2. The method according to claim 1, wherein the step of inserting the E-field probe is done under ultrasound guidance to the central depth of the breast tissue or in a breast lesion.

3. The method according to claim 2, further comprising the steps of compressing the breast between 3 cm and 8 cm with compression plates; and adjusting the amount of breast compression during treatment for patient comfort; and wherein the breast compression plates are made of plastic and have a thickness between 2 mm and 4 mm and contain one or more apertures of 4.5 to 6.5 cm diameter to allow imaging of breast tissues and placement of the E-field probe with an ultrasound transducer.

4. The method according to claim 1, wherein the step of monitoring the skin surface temperature includes the step of attaching temperature probe sensors to the skin surface of the breast.

5. The method according to claim 1, wherein the cancerous conditions of the breast include invasive ductal carcinoma, pre-cancerous conditions including ductal carcinoma in-situ, lobular carcinoma in-situ, and intraductal hyperplasia cells, and benign breast lesions including fibroadenomas and cysts.

6. The method according to claim 1, further including the step of adjusting air flow from individual fans surrounding the breast to cool the breast skin surface, wherein the air is one of air-conditioned, refrigerated or room-temperature and the air flow goes through or around the microwave applicators.

7. The method according to claim 1, wherein the frequency of the microwave energy is between 100 MHz and 10 GHz.

8. The method according to claim 1, further comprising the step of adjusting the relative microwave phase delivered to the two microwave waveguide applicators; and wherein the relative phase is adjusted between −180 degrees and 180 degrees before and during the treatment to create a focused field in the breast tissue.

9. The method according to claim 1, wherein the initial microwave power delivered to each microwave applicator is between 20 Watts and 60 Watts.

10. The method according to claim 1, wherein the microwave power delivered to each microwave applicator is adjusted over the range of 0 to 150 Watts during the treatment to deliver the desired microwave energy dose and to avoid overheating the skin.

11. The method according to claim 1, wherein the total microwave energy delivered to the microwave applicators for complete treatment is between 25 kilojoules and 250 kilojoules.

12. The method according to claim 1, further comprising the step of inserting a temperature probe sensor to monitor temperature at an appropriate depth in the breast tissue.

13. The method according to claim 1, wherein the total microwave energy dose produces a total equivalent thermal dose in the breast lesions which is approximately between 40 minutes and 100 minutes relative to 43 degrees Celsius.

14. The method according to claim 1, further comprising the step of monitoring the microwave power level delivered to the E-field probe wherein the total microwave energy received by the E-field probe is used as feedback to determine the length of treatment.

15. The method according to claim 1, wherein for large breast tumors much of the treated breast carcinomas are destroyed as a result of the heat treatment from steps a–h and the tumor shrinks sufficiently so that a surgical lumpectomy can be performed instead of a surgical mastectomy; and
   wherein the heat treatment from steps a–h avoids damage to normal tissue of the breast.

16. The method of claim 1, wherein all of the treated breast carcinomas and other lesions are destroyed as a result of the heat treatment from steps a–h, such that a surgical mastectomy or lumpectomy is no longer deemed medically necessary based on mammography means including x-ray, ultrasound, and magnetic resonance imaging before and after the microwave total energy dose is administered; and wherein the heat treatment from steps a–h avoids damaging normal tissue of the breast.

17. The method according to claim 1, wherein steps a–h are repeated a number of times until all of the breast lesions (cancerous, pre-cancerous, and benign) have been completely destroyed as a result of the heat treatments without damage to normal tissue of the breast.

18. The method of claim 1 whereby the focused microwave radiation is used to enhance radiation therapy or for targeted drug delivery and targeted gene therapy with thermosensitive liposomes for treatment of breast tumors and other breast lesions.

19. A method for treating cancerous or benign conditions of the breast by selective irradiation of the breast tissue with focused microwave energy, the method comprising the steps of:
 a) Inserting an E-field probe sensor to an appropriate depth in the breast tissue;
 b) Monitoring temperatures of the breast skin surface;
 c) Orienting two microwave applicators on opposite sides of the breast;
 d) Setting the initial microwave power delivered to each microwave applicator;
 e) Setting the initial relative microwave phase delivered to each microwave applicator to focus the microwave energy at the E-field probe positioned in the breast tissue;
 f) Adjusting the relative microwave power to be delivered to the breast during treatment based on the monitored skin temperatures;
 g) Monitoring the microwave energy delivered to the microwave waveguide applicators;
 h) Determining total microwave energy delivered to the microwave applicators and displaying the total microwave energy in real time during the treatment; and
 i) Completing the treatment when the desired total microwave energy dose has been delivered by the microwave applicators to the breast.

20. A method for treating cancerous or benign conditions of the breast by selective irradiation of the breast tissue with focused microwave energy, the method comprising the steps of:
 a) Positioning two noninvasive E-field skin probes an opposite sides of the breast skin surface,
 b) Monitoring temperatures of the skin surface;
 c) Orienting two microwave applicators on opposite sides of the breast;
 d) Setting the initial microwave power delivered to each microwave applicator;
 e) Setting the initial relative microwave phase delivered to each microwave applicator to focus the microwave energy at the breast tissue to be treated;
 f) Adjusting the microwave phase delivered to each microwave applicator to minimize the total power received by the E-field skin probes thereby creating a focused field in the breast;
 g) Adjusting the relative microwave power to be delivered to each microwave applicator during treatment based on the monitored skin temperatures;
 h) Monitoring the microwave energy delivered to the microwave applicators; and
 i) Completing the treatment when a desired total microwave energy dose has been delivered by the microwave applicators to the breast.

21. A method for preventing the occurrence or recurrence of cancerous or benign conditions by selectively heating or irradiating healthy tissue with focused microwave energy, the method comprising the steps of:
 a) Inserting an E-field probe sensor to an appropriate depth in the breast tissue;
 b) Monitoring temperatures of the skin surface;
 c) Orienting two microwave waveguide applicators on opposite sides of the breast;
 d) Delivering microwave energy/power with a relative microwave phase to each microwave waveguide applicator to focus the microwave energy at the E-field probe;
 e) Adjusting the relative microwave power to be delivered to each microwave waveguide applicator during treatment based on the monitored skin temperatures;
 f) Monitoring the microwave energy delivered to the microwave waveguide applicators; and
 g) Completing the treatment when a desired total microwave energy dose has been delivered by the microwave waveguide applicators to the treated tissue.

22. A method for treating cancerous or benign conditions of the breast by selective irradiation of the breast tissue with focused microwave energy, the method comprising the steps of:
 a) Inserting an E-field probe sensor to an appropriate depth in the breast tissue;
 b) Monitoring temperatures of the skin surface;
 c) Orienting two microwave waveguide applicators on opposite sides of the breast for irradiating the breast with microwave energy;
 d) Delivering microwave energy/power with a relative microwave phase to each microwave waveguide applicator to focus the microwave energy based on the position of the E-field probe;
 e) Adjusting the relative microwave power to be delivered to each microwave waveguide applicator during treatment based on the monitored skin temperatures;
 f) Determining boundary points about the E-field probe to obtain a geometric shape for irradiating the breast; and
 g) Adjusting the relative phase of the microwave energy applied to each microwave waveguide applicator so that the applied focused microwave energy scans the determined geometric shape thereby irradiating a larger area of the breast.

23. A method for treating cancerous or benign conditions of the breast by selective irradiation of the breast tissue with focused microwave energy, the method comprising the steps of:
 a) Inserting an E-field probe sensor to an appropriate depth in the breast tissue;
 b) Inserting a temperature probe sensor to monitor temperature at an appropriate depth in the breast tissue;
 c) Monitoring temperatures of the skin surface;
 d) Orienting two microwave applicators on opposite sides of the breast;
 e) Setting the initial microwave power delivered to each microwave applicator;
 f) Setting the initial relative microwave phase delivered to each microwave applicator to focus the microwave energy at the E-field probe positioned in the breast tissue;
 g) Adjusting the relative microwave power to be delivered to the breast during treatment based on the monitored internal skin temperature, the monitored skin temperatures, and the monitored microwave energy dose; and h) Completing the treatment when one of a desired total microwave energy dose and a desired thermal dose has been delivered by the microwave applicators to the breast.

24. A method for treating cancerous or benign conditions of the breast by selective irradiation of the breast tissue with focused microwave energy, the method comprising the steps of:

a) Positioning two noninvasive E-field skin probes on opposite sides of the breast skin surface;
   b) Inserting a temperature probe sensor to monitor temperature at an appropriate depth in the breast tissue;
   c) Monitoring temperatures of the skin surface;
   d) Orienting two microwave applicators on opposite sides of the breast;
   e) Setting the initial microwave power delivered to each microwave applicator;
   f) Setting the initial relative microwave phase delivered to each microwave applicator to focus the microwave energy at the breast tissue to be treated;
   g) Adjusting the microwave phase delivered to each microwave waveguide applicator to minimize the total power received by the E-field skin probes thereby creating a focused field in the breast;
   h) Adjusting the microwave power to be delivered to the breast during treatment based on the monitored internal breast tissue temperature, the monitored skin temperatures, and the monitored microwave energy dose; and
   i) Completing the treatment when one of a desired total microwave energy dose and a desired thermal dose has been delivered by the microwave applicators to the breast.

25. A method for treating cancerous or benign conditions of the breast by selective irradiation of the breast tissue with focused microwave energy, the method comprising the steps of:

a) Inserting an E-field probe sensor to an appropriate depth in the breast tissue;
   b) Monitoring temperatures at an appropriate depth in the breast tissue and on the skin surface by means of noninvasive thermometry techniques including one of infrared, laser, ultrasound, electrical impedance tomography, magnetic resonance imaging, and radiometry;
   c) Orienting two microwave applicators on opposite sides of the breast;
   d) Setting the initial microwave power delivered to each microwave applicator;
   e) Setting the initial relative microwave phase delivered to each microwave applicator to focus the microwave energy at the E-field probe positioned in the breast tissue;
   f) Adjusting the relative microwave power to be delivered to the breast during treatment based on the monitored internal temperature, the monitored skin temperatures, and the monitored microwave energy dose; and
   g) Completing the treatment when one of a desired total microwave energy doses and a desired thermal dose has been delivered by the microwave applicators to the breast.

26. A method for treating cancerous or benign conditions of the breast by selective irradiation of the breast tissue with focused microwave energy, the method comprising the steps of:

a) Positioning two noninvasive E-field skin probes on opposite sides of the breast skin surface;
   b) Monitoring temperatures at an appropriate depth in the breast tissue and on the skin surface by means of noninvasive thermometry techniques including one of infrared, laser, ultrasound, electrical impedance tomography, magnetic resonance imaging, and radiometry;
   c) Orienting two microwave applicators on opposite sides of the breast;
   d) Setting the initial microwave power delivered to each microwave applicator;
   e) Setting the initial relative microwave phase delivered to each microwave applicator to focus the microwave energy at the breast tissue to be treated;
   f) Adjusting the microwave phase delivered to each microwave applicator to minimize the total power received by the E-field skin probes thereby creating a focused field in the breast;
   g) Adjusting the microwave power to be delivered to the breast during treatment based on the monitored internal breast tissue temperature, the monitored skin temperatures, and the monitored microwave energy dose; and
   h) Completing the treatment when one of a desired total microwave energy dose and a desired thermal dose has been delivered by the microwave applicators to the breast.

27. A method for treating tumors and other lesions in a body comprising the steps of:

a) Compressing tissue and injecting a drug in an area where a tumor is located and monitored by Doppler ultrasound or microwave, said compression and drug reducing blood flow to allow rapid heating of tumors and other lesions, said drug including a local anesthetic with ephinephrine or an anti-angiogenesis drug; and
   b) heating the tumor and other lesions with one of microwave, ultrasound, radiofrequency, and laser energy.

28. A method for treating cancerous or benign conditions of the breast by selective irradiation of the breast tissue with focused microwave energy, the method comprising the steps of:

a) Inserting an E-field probe sensor to an appropriate depth in the breast tissue;
   b) Monitoring temperatures of the breast skin surface;
   c) Orienting two microwave applicators on opposite sides of the breasts;
   d) Setting the initial microwave power delivered to each microwave applicator;
   e) Setting the initial relative microwave phase delivered to each microwave applicator to focus the microwave energy at the E-field probe position in the breast tissue;
   f) Adjusting the relative microwave power to be delivered to each microwave applicator during treatment based on the monitored skin temperatures;

g) Monitoring the microwave energy delivered to the microwave applicators; and h) Completing the treatment when a desired total microwave energy dose has been delivered by the microwave applicators to the breast, wherein the total microwave energy delivered to the microwave applicator for complete treatment is between 25 kilojoules and 250 kilojoules.

* * * * *